US009402917B2

(12) United States Patent
Alam et al.

(10) Patent No.: US 9,402,917 B2
(45) Date of Patent: Aug. 2, 2016

(54) METHODS FOR THE INDUCTION OF BROADLY ANTI-HIV-1 NEUTRALIZING ANTIBODY RESPONSES EMPLOYING LIPOSOME-MPER PEPTIDE COMPOSITIONS

(75) Inventors: S. Munir Alam, Durham, NC (US); Barton F. Haynes, Durham, NC (US); Moses D. Sekaran, Durham, NC (US); Georgia Tomaras, Durham, NC (US); Xiaoying Shen, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 213 days.

(21) Appl. No.: 13/262,706

(22) PCT Filed: Apr. 5, 2010

(86) PCT No.: PCT/US2010/001017

§ 371 (c)(1), (2), (4) Date: Feb. 1, 2012

(87) PCT Pub. No.: WO2010/114628

PCT Pub. Date: Oct. 7, 2010

(65) Prior Publication Data

US 2012/0128758 A1 May 24, 2012

Related U.S. Application Data

(60) Provisional application No. 61/166,625, filed on Apr. 3, 2009.

(51) Int. Cl.

| | |
|---|---|
| ***A61K 39/385*** | (2006.01) |
| ***A61K 38/21*** | (2006.01) |
| ***A61P 31/18*** | (2006.01) |
| ***A61K 9/127*** | (2006.01) |
| ***A61K 47/48*** | (2006.01) |
| ***A61K 39/21*** | (2006.01) |
| ***A61K 39/12*** | (2006.01) |
| *A61K 39/00* | (2006.01) |

(52) U.S. Cl.

CPC ......... *A61K 47/48815* (2013.01); *A61K 38/212* (2013.01); *A61K 39/12* (2013.01); *A61K 39/21* (2013.01); *A61K 47/4833* (2013.01); *A61K 9/1272* (2013.01); *A61K 2039/545* (2013.01); *A61K 2039/55511* (2013.01); *A61K 2039/55555* (2013.01); *A61K 2039/55561* (2013.01); *A61K 2039/55572* (2013.01); *C12N 2740/16134* (2013.01)

(58) Field of Classification Search

CPC . A61K 47/48815; A61K 39/12; A61K 39/21; A61K 2039/55572; A61K 2039/55555; C12N 2740/16134

See application file for complete search history.

(56) References Cited

U.S. PATENT DOCUMENTS

| | | | |
|---|---|---|---|
| 5,707,626 | A | 1/1998 | Douvas et al. |
| 5,919,459 | A | 7/1999 | Nacy et al. |
| 6,156,337 | A | 12/2000 | Barenholz et al. |
| 2006/0089326 | A1 | 4/2006 | Krieg et al. |
| 2008/0031890 | A1 | 2/2008 | Haynes et al. |
| 2008/0057075 | A1 | 3/2008 | Haynes |
| 2009/0035360 | A1 | 2/2009 | Lemoine |
| 2010/0028415 | A1 | 2/2010 | Haynes et al. |
| 2010/0047331 | A1 | 2/2010 | Haynes et al. |
| 2012/0070488 | A1 | 3/2012 | Haynes et al. |
| 2012/0183597 | A1 | 7/2012 | Haynes et al. |
| 2013/0323299 | A1 | 12/2013 | Haynes et al. |
| 2014/0322262 | A1 | 10/2014 | Spicer et al. |
| 2015/0147387 | A1 | 5/2015 | Haynes et al. |

FOREIGN PATENT DOCUMENTS

| | | | |
|---|---|---|---|
| EP | 1250933 | A1 | 10/2002 |
| JP | 2006-512391 | A | 4/2006 |
| WO | WO-95/25124 | A1 | 9/1995 |
| WO | WO-2004/087738 | A2 | 10/2004 |
| WO | WO-2006/110831 | A2 | 10/2006 |
| WO | 2008127651 | A1 | 10/2008 |
| WO | WO-2009/111304 | A2 | 9/2009 |
| WO | WO-2010/042942 | A2 | 4/2010 |
| WO | WO-2010/045613 | A1 | 4/2010 |
| WO | WO-2010/114628 | A2 | 10/2010 |
| WO | WO-2010/114629 | A2 | 10/2010 |

OTHER PUBLICATIONS

Huarte, N., et al., Sep. 2008, The broadly neutralizing anti-human immunodeficiency virus type 1 4E10 monoclonal antibody is better adapted to membrane-bound epitope recognition and blocking than 2F5, J. Virol. 82(18):8986-8996.*

International Search Report for PCT/US2010/001017, mailed Jan. 18, 2011.

Written Opinion of the International Searching Authority for PCT/US2010/001017, mailed Jan. 18, 2011.

Huarte, N. et al., "The Broadly Neutralizing Anti-Human Immunodeficiency Virus Type 1 4E10 Monoclonal Antibody is Better Adapted to Membrane-Bound Epitope Recognition and Blocking than 2F5", J. Virol., vol. 82(18), pp. 8986-8996, (Jul. 2, 2008).

Alam, S. M. et al, "The Role of Antibody Polyspecificity and Lipid Reactivity in Binding of Broadly Neutralizing Anti-HIV-1 Envelope Human Monoclonal Antibodies 2F5 and 4EIO to Glycoprotein 41 Membrane Proximal Envelope Epitopes," The Journal of Immunology, vol. 178, No. 7, pp. 4424-4435, 25 pages (Apr. 1, 2007).

(Continued)

*Primary Examiner* — Jeffrey Parkin

(74) *Attorney, Agent, or Firm* — Wilmer Cutler Pickering Hale and Dorr LLP

(57) ABSTRACT

The present invention relates in general, to a formulation suitable for use in inducing anti-HIV-1 antibodies, and, in particular, to a formulation comprising Toll Like Receptor (TLR) agonists with HIV-1 gp41 membrane proximal external region (MPER) peptide-liposome conjugates for induction of broadly reactive anti-HIV-1 antibodies. The invention also relates to methods of inducing neutralizing anti-HIV-1 antibodies using such formulations.

28 Claims, 17 Drawing Sheets

(56) References Cited

OTHER PUBLICATIONS

Alam, S. M. et al., "An Inducible HIV Type 1 gp41 HR-2 Peptide-Binding Site on HIV Type 1 Envelope gp120," Aids Research and Human Retroviruses, vol. 20, No. 8, pp. 836-845 (Aug. 2004).
Alam, S. M. et al., "Human Immunodeficiency Virus Type 1 gp41 Antibodies That Mask Membrane Proximal Region Epitopes: Antibody Binding Kinetics, Induction, and Potential for Regulation in Acute Infection," Journal of Virology, vol. 82, No. 1, pp. 115-125 (Jan. 2008).
Alving, C. R. et al., "HIV-1, Lipid Rafts, and Antibodies to Liposomes: Implications for Anti-Viral-Neutralizing Antibodies," Molecular Membrane Biology, vol. 23, No. 6, pp. 453-465 (Nov. 1, 2006).
Alving, C. R. et al., "Immunologic aspects of liposomes: presentation and processing of liposomal protein and phospholipid antigens," Biochimica et Biophysica Acta, vol. 1113, No. 3-4, pp. 307-322 (Dec. 11, 1992).
Cardoso, R. M. et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Chen, X. et al., "Novel recombinant engineered gp41 N-terminal heptad repeat trimers and their potential as anti-HIV-1 therapeutics or microbicides," The Journal of Biological Chemistry, vol. 285, No. 33, pp. 25506-25515 (Aug. 13, 2010) (23 pages).
Coeffier, E. et al., "Antigenicity and immunogenicity of the HIV-1 gp41 epitope ELDKWA inserted into permissive sites of the MalE protein," Vaccine, vol. 19, No. 7-8, pp. 684-693 (Nov. 22, 2000).
Frey, G. et al., "A fusion-intermediate state of HIV-1 gp41 targeted by broadly neutralizing antibodies," PNAS, vol. 105, No. 10, pp. 3739-3744 (Mar. 11, 2008).
Frisch, B. et al., "Synthetic peptide-based highly immunogenic liposomal constructs," Methods in Enzymology, vol. 373, pp. 51-73 (2003).
Haynes, B. F. et al., "Cardiolipin polyspecific autoreactivity in two broadly neutralizing HIV-1 antibodies," Science, vol. 308, No. 5730, pp. 1906-1908 (Jun. 24, 2005).
Hinz, A. et al., "Characterization of a trimeric MPER containing HIV-1 gp41 antigen," Virology, vol. 390, No. 2, pp. 221-227 (Aug. 1, 2009).
Ho, J. et al., "Conformational constraints imposed on a pan-neutralizing HIV-1 antibody epitope result in increased antigenicity but not neutralizing response," Vaccine, vol. 23, pp. 1559-1573 (2005).
International Preliminary Report on Patentability issued by the International Bureau of WIPO for International Application No. PCT/US2006/013684 dated Apr. 28, 2009 (4 pages).
International Preliminary Report on Patentability issued by the International Bureau of WIPO for International Application No. PCT/US2008/004709 dated Oct. 13, 2009 (5 pages).
International Preliminary Report on Patentability issued by the International Bureau of WIPO for International Application No. PCT/US2012/032717 dated Oct. 8, 2013 (5 pages).
International Search Report and Written Opinion issued by the Korean Intellectual Property Office as International Searching Authority for International Application No. PCT/US2012/032717 dated Oct. 29, 2012 (8 pages).
International Search Report and Written Opinion issued by the U.S. Patent and Trademark Office as International Searching Authority for International Application No. PCT/US06/13684 dated Jul. 31, 2008 (4 pages).
International Search Report and Written Opinion issued by the U.S. Patent and Trademark Office for International Application No. PCT/US2008/04709 dated Sep. 17, 2008 (7 pages).
Japanese Office Action issued by the Japan Patent Office for Japanese Application No. 2012-503432 dated Jun. 16, 2014 (4 pages—English translation only).
Jing, L. et al., "The interaction between the membrane-proximal external region and the N-trimer region of HIV-1 gp41: Involvement in viral fusion," Chinese Science Bulletin, vol. 54, No. 10, pp. 1707-1712 (May 2009).
Joyce, J. G. et al., "Enhancement of alpha —helicity in the HIV-1 inhibitory peptide DP178 leads to an increased affinity for human monoclonal antibody 2F5 but does not elicit neutralizing responses in vitro. Implications for vaccine design," J. Biol. Chem., vol. 277, No. 48, pp. 45811-45820 (Nov. 29, 2002).
Kim, M., et al. "Immunogenicity of recombinant human immunodeficiency virus type 1-like particles expressing gp41 derivatives in a pre-fusion state," Vaccine, vol. 25, No. 27, pp. 5102-5114, 24 pages (Jun. 28, 2007).
Mehandru, S. et al., "Neutralization Profiles of Newly Transmitted Human Immunodeficiency Virus Type 1 by Monoclonal Antibodies 2G12, 2F5, and 4E10," Journal of Virology, vol. 78, No. 24, pp. 14039-14042 (Dec. 2004).
Muster, T. et al., "Cross-neutralizing activity against divergent human immunodeficiency virus type 1 isolates induced by the gp41 sequence ELDKWAS," Journal of Virology, vol. 68, No. 6, pp. 4031-4034 (Jun. 1994).
Nelson, J. D. et al., "An affinity-enhanced neutralizing antibody against the membrane-proximal external region of human immunodeficiency virus type 1 gp41 recognizes an epitope between those of 2F5 and 4E10," J. Virol., vol. 81, No. 8, pp. 4033-4043 (Apr. 2007).
Ofek, G. et al, "Structure and Mechanistic Analysis of the Anti-Human Immunodeficiency Virus Type I Antibody 2F5 in complex with Its gp41 Epitope," Journal of Virology, vol. 78, No. 19, pp. 10724-10737 (Oct. 2004).
Ou, W. et al., "Effect of epitope position on neutralization by anti-human immunodeficiency virus monoclonal antibody 2F5," J. Virol., vol. 80, No. 5, pp. 2539-2547 (Mar. 2006).
Petrovas, C. et al., "Anti-phospholipid antibodies in HIV infection and SLE with or without anti-phospholipid syndrome: comparisons of phospholipid specificity, avidity and reactivity with beta2- GPI," Journal of Autoimmunity, vol. 13, No. 3, pp. 347-355 (Nov. 1999).
Purtscher, M. et al., "Restricted antigenic variability of the epitope recognized by the neutralizing gp41 antibody 2F5," AIDS, vol. 10, No. 6, pp. 587-593 (Jun. 1996).
Reardon, P. N. et al., "Structure of an HIV-1-neutralizing antibody target, the lipid-bound gp41 envelope membrane proximal," PNAS, vol. 111, No. 4, pp. 1391-1396, 10 pages. (Jan. 28, 2014).
Sakaue, G. et al., "HIV mucosal vaccine: nasal immunization with gp160-encapsulated hemagglutinating virus of Japan-liposome induces antigen-specific CTLs and neutralizing antibody responses," Journal of Immunology, vol. 170, No. 1, pp. 495-502 (Jan. 1, 2003).
Sanchez, P. J. et al., "Combined TLR/CD40 Stimulation Mediates Potent Cellular Immunity by Regulating Dendritic Cell Expression of CD70 In Vivo," the Journal of Immunology, vol. 178, No. 3, pp. 1564-1572 (Feb. 1, 2007).
Shen, X. et al., "In vivo gp41 antibodies targeting the 2F5 monoclonal antibody epitope mediate human immunodeficiency virus type 1 neutralization breadth," J. Virol., vol. 83, No. 8, pp. 3617-3625 (Apr. 2009).
Shen, X. et al., "Prolonged exposure of the HIV-1 gp41 membrane proximal region with L669S • substitution," PNAS, vol. 107, No. 13, pp. 5972-5977 (Mar. 30, 2010).
Supplementary European Search Report issued by the European Patent Office for Application No. 08742782.9 dated May 31, 2011 (11 pages).
Supplementary European Search Report issued by the European Patent Office for Application No. EP 12768170.8 dated Sep. 2, 2010 (5 pages).
Supplementary European Search Report issued by the European Patent Office for Application No. EP06740904 dated Sep. 2, 2010 (16 pages).
Zhang, G. et al., "Neutralization of HIV-1 primary isolate by ELDKWA-specific murine monoclonal antibodies," Immunobiology, vol. 210, No. 9, pp. 639-645 (2005).
Zhang, M.Y. et al., "Cross-Reactive Human Immunodeficiency Virus Type 1-Neutralizing Human Monoclonal Antibody That Recognizes a Novel Conformational Epitope on gp41 and Lacks Reactivity against Self-Antigens," Journal of Virology, vol. 82, No. 14, pp. 6869-6879 (Jul. 2008).
Zwick, M. B. et al, "Anti-Human Immunodeficiency Virus Type I (HIV-1) Antibodies 2F5 and 4E10 Require Surprisingly Few Crucial

(56) References Cited

OTHER PUBLICATIONS

Residues in the Membrane-Proximal External Region of Glycoprotein gp41 to Neutralize HIV-1," Journal of Virology, vol. 79, No. 2, pp. 1252-1261 (Jan. 2005).

Zwick, M. B. et al., "The Long Third Complementarity-Determining Region of the Heavy Chain is Important in the Activity of the Broadly Neutralizing Anti-Human Immunodeficiency Virus Type 1 Antibody 2F5," Journal of Virology, vol. 78, No. 6, pp. 3155-3161 (Mar. 2004).

Zwick, M. B. et al., "Broadly neutralizing antibodies targeted to the membrane-proximal external region of human immunodeficiency virus type 1 glycoprotein gp41," J. Virol., vol. 75, No. 22, pp. 10892-10905 (Nov. 2001).

Notification of Reasons for Rejection mailed on Jun. 16, 2014 in Japanese application No. 2012-503432, 4 pages.

Extended European Search Report mailed on Apr. 20, 2015 in European application No. 10759166.1, 6 pages.

* cited by examiner

| Target/nature of agent | | TND_669S | TND_669L | | |
|---|---|---|---|---|---|
| MPER | 2F5 | 0.014 | 3.915 | 279x | ✓ |
| MPER | 4E10 | 0.031 | 8.054 | 275x | ✓ |
| IgG1b12, 2G12, 2F5 | TriMab | 0.030 | 2.866 | 102x | |
| CD4 binding site | 1b12 | 0.53 | 2.06 | 3.9x | |
| Glycan dependent | 2G12 | 12.5 | 16.68 | 1.3x | |
| Fusion Inhibitor | T20 | 0.020 | 0.0545 | 2.8x | |
| CD4i | 17b | 9.73 | 19 | 2.0x | |
| CD4i: CCR5 binding Site | 1.7B | 27.5 | >50 | >1.8 | |
| CD4i | 23E | 24.5 | >50 | >2.0 | |
| CD4i: CCR5 binding Site | E51 | 7.6 | >50 | >6.6 | |
| V3 loop | 447-52D | 0.31 | >50 | >161 | ✓ |

| | 2F5 IC50 (μg/ml) | |
|---|---|---|
| Peptide Conc. | conensus peptide* | mutant peptide |
| 30 μM | >2.5 | >2.5 |
| 3 μM | >2.5 | 0.951 |
| 0.3 μM | 0.911 | 0.153 |
| 0 μM | 0.054 | 0.056 |

* Previously reported (reference Shen, et. al. submitted)

$$A + B \underset{k_d1}{\overset{k_a1}{\rightleftharpoons}} AB \text{ (encounter)} \underset{k_d2}{\overset{k_a2}{\rightleftharpoons}} ABx \text{ (docked)}$$

| | $k_a1$ $10^5\ M^{-1}\ s^{-1}$ | $k_d1$ $10^{-3}\ s^{-1}$ | $k_a2$ $10^{-2}\ s^{-1}$ | $k_d2$ $10^{-4}\ s^{-1}$ |
|---|---|---|---|---|
| 2F5 peptide liposome | 9.31 | 6.92 | 1.81 | 3.70 |
| L669S 2F5 peptide liposome | 4.98 | 1.19 | 0.54 | 0.20 |

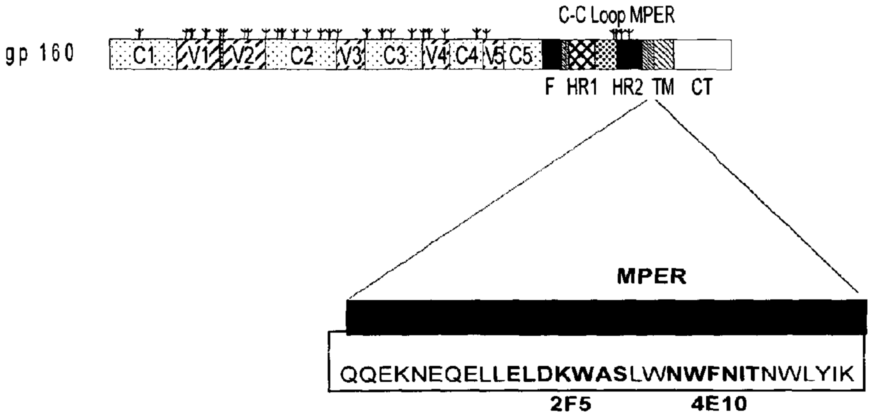

MPER peptides:
SP62 QQEKNEQELLELDKWASLWN
gp41 652-671
SP62-L669S QQEKNEQELLELDKWASSWN
MPER656 gp41656-683 NEQELLELDKWASLWNWFNITNWLWYIK
MPER656-L669S NEQELLELDKWASSWNWFNITNWLWYIK
gp41 656-683

Scheme 1. HIV-1 gp41 MPER peptides that include the epitopes of the two broadly neutralizing antibodies 2F5 and 4E10. Amino acid sequences of the gp41 MPER peptides that can be conjugated to synthetic liposomes are shown.

Fig. 8

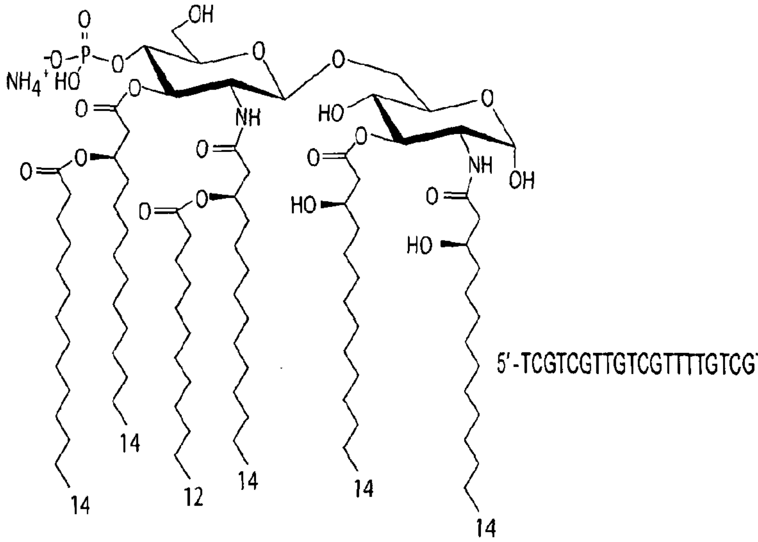
5'-TCGTCGTTGTCGTTTTGTCGTT-3'
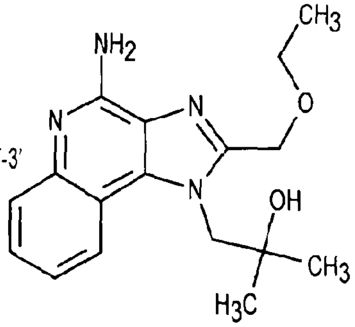
Lipid A (monophosphoryl)
Oligo CpG
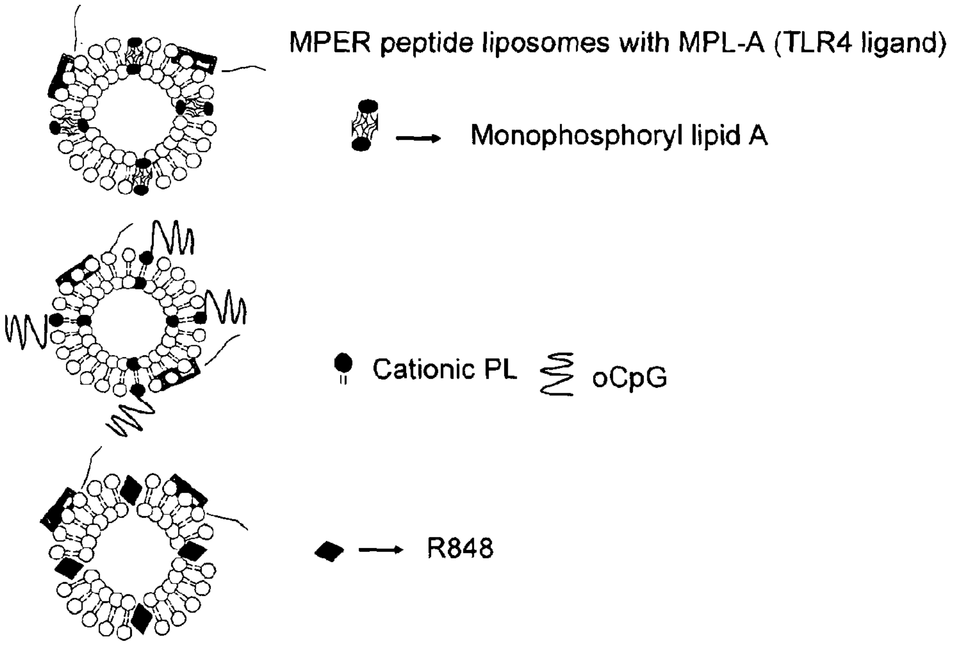
Structures of TLR agonists formulated with liposomes.
Fig. 9

Interaction of 2F5 mAb with MPER peptide-liposomes conjugated to TLR adjuvants.

MPER peptide liposomes with MPL-A (TLR 4 ligand)

Monophosphoryl lipid A oCpG (TLR9 ligand) conjugated MPER peptide liposomes

● Cationic PL    ⋛ oCpG

MPER peptide liposomes with R848 (TLR 7/8 ligand)

IFNα encapsulated MPER peptide liposomes

B cell responses via dual TLR triggering.

IFNα encapsulated liposome with multiple TLR ligands. These constructs have the potential to provide synergy in

| | | | | | |
|---|---|---|---|---|---|
| Mutants: | 2F5-mut1 rIgG | L100aA | Mutants: | 4E10-mut1 scFv | W100A |
| | 2F5-mut2 rIgG | F100bA | | 4E10-mut2 scFv | F100bA |
| | 2F5-mut3 rIgG | L100aA/100bB | | 4E10-mut3 scFv | W100A/W100bA/L100cA |
| | 2F5-mut4 rIgG | R95A | | 4E10-mut4 scFv | 156A/S94R |

Crystal structures of 2F5 (Ofek et al, 2004, , J. Virol., 78:10724) and 4E10 (Cardoso et al., 2005, Immunity, 22:163-173) and design of mutations in the CDR H3 loop to eliminate binding to lipids and HIV-1 viral membrane

4E10

| | gp41 Binding | | | |
|---|---|---|---|---|
| | peptide | gp41-inter | Viral membrane | Neutralization |
| 4E10 scFv-WT | +++ | +++ | +++ | +++ |
| Mut 4: S(L94)R; I(H56)A | + | ++ | +++ | ++ |
| Mut 1:W(H100)A | ++ | ++ | + | ++ |
| Mut 2:W(H100)A; W(H100b)A | ++ | ++ | – | – |
| Mut 3: W(H100)A; W(H100b)A; L(H100c)A | + | ++ | – | – |

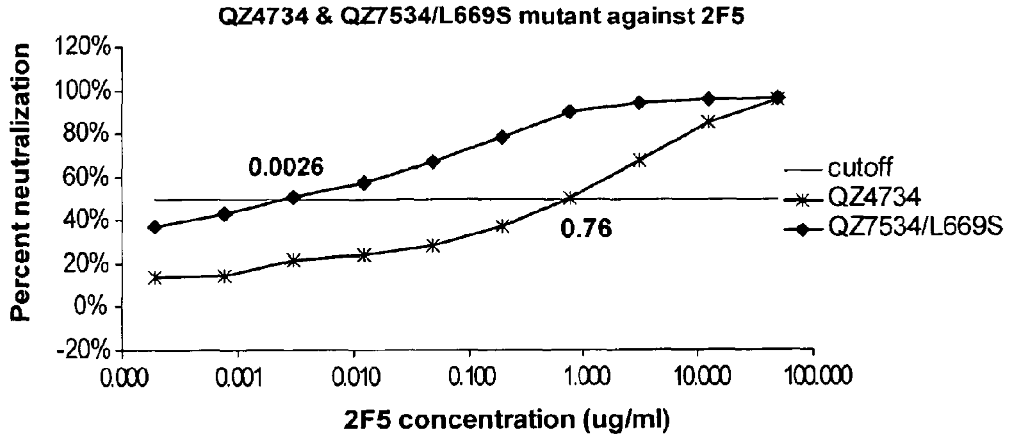

Neutralization of QZ4734 and QZ4734/L669S pseudotyped viruses by 2F5 mAb (tested on TZM-bl cells). QZ4734/L669S was generated by introducing L669S single mutation into the QZ4734 envelope. Numbers by the curves indicate the IC50 values.

Fig. 15

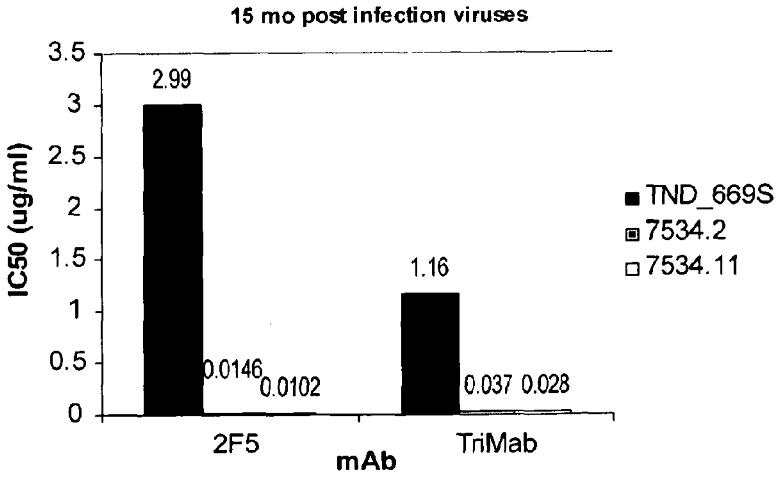

Neutralization of TND_669S and two other stains (7534.2 and 7534.11) isolated from the same plasma sample (15 mo post infection) by 2F5 and TriMab (1:1:1 combination of 2F5, 4E10 and 2G12). Numbers above each bar represents IC50 values. The test was performed on TZM-bl cells.

Fig. 16

Induction of gp41 MPER (membrane proximal external region) specific antibody responses in guinea pigs immunized with MPER liposomal immunogens.

Induction of gp41 MPER (membrane proximal external region) specific antibody responses in Non human primates (NHP) immunized with MPER liposomal immunogens.

SEQUENCE LISTING

```
<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

tagagccctg gaagcatcca ggaag                                        25


<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

ttgctacttg tgattgctcc atgt                                         24
```

-continued

```
<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

cacctaggca tctcctatgg caggaagaag                                    30


<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gtctcgagat actgctccca ccc                                           23


<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

ggataagtgg gcaagtttgt ggaattggtt tgac                               34


<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

gtcaaaccaa ttccacaaac ttgcccactt atcc                               34


<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

gaattattag aattggataa ctgggcaagt tcgtgg                             36


<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

ccacgaactt gcccagttat ccaattctaa taattc                             36


<210> SEQ ID NO 9
```

-continued

<211> LENGTH: 20
<212> TYPE: PRT
<213> ORGANISM: Human immunodeficiency virus 1

<400> SEQUENCE: 9

Gln Gln Glu Lys Asn Glu Gln Glu Leu Leu Glu Leu Asp Lys Trp Ala
1 5 10 15

Ser Leu Trp Asn
20

<210> SEQ ID NO 10
<211> LENGTH: 20
<212> TYPE: PRT
<213> ORGANISM: Human immunodeficiency virus 1

<400> SEQUENCE: 10

Gln Gln Glu Lys Asn Glu Gln Glu Leu Leu Glu Leu Asp Lys Trp Ala
1 5 10 15

Ser Ser Trp Asn
20

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Gln Glu Lys Asn Glu Gln Glu Leu Leu Glu Leu Asp Lys Trp Ala
1 5 10 15

Ser Leu Trp Asn Tyr Lys Arg Trp Ile Ile Leu Gly Leu Asn Lys Ile
20 25 30

Val Arg Met Tyr Ser
35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Gln Gln Glu Lys Asn Glu Gln Glu Leu Leu Glu Leu Asp Lys Trp Ala
1 5 10 15

Ser Ser Trp Asn Tyr Lys Arg Trp Ile Ile Leu Gly Leu Asn Lys Ile
20 25 30

Val Arg Met Tyr Ser
35

<210> SEQ ID NO 13
<211> LENGTH: 15
<212> TYPE: PRT
<213> ORGANISM: Human immunodeficiency virus 1

<400> SEQUENCE: 13

Glu Gln Glu Leu Leu Glu Leu Asp Lys Trp Ala Ser Leu Trp Asn
1 5 10 15

<210> SEQ ID NO 14

-continued

```
<211> LENGTH: 6
<212> TYPE: PRT
<213> ORGANISM: Human immunodeficiency virus 1

<400> SEQUENCE: 14

Glu Leu Asp Lys Trp Ala
1               5


<210> SEQ ID NO 15
<211> LENGTH: 6
<212> TYPE: PRT
<213> ORGANISM: Human immunodeficiency virus 1

<400> SEQUENCE: 15

Asn Trp Phe Asn Ile Thr
1               5


<210> SEQ ID NO 16
<211> LENGTH: 28
<212> TYPE: PRT
<213> ORGANISM: Human immunodeficiency virus 1

<400> SEQUENCE: 16

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25


<210> SEQ ID NO 17
<211> LENGTH: 28
<212> TYPE: PRT
<213> ORGANISM: Human immunodeficiency virus 1

<400> SEQUENCE: 17

Asn Glu Gln Glu Leu Leu Glu Leu Asp Lys Trp Ala Ser Ser Trp Asn
1               5                   10                  15

Trp Phe Asn Ile Thr Asn Trp Leu Trp Tyr Ile Lys
            20                  25


<210> SEQ ID NO 18
<211> LENGTH: 52
<212> TYPE: PRT
<213> ORGANISM: Human immunodeficiency virus 1

<400> SEQUENCE: 18

Asp Tyr Ile Tyr Ser Leu Leu Glu Asn Ala Gln Asn Gln Gln Glu Arg
1               5                   10                  15

Asn Glu Gln Glu Leu Leu Glu Leu Asp Lys Trp Ala Ser Leu Trp Asn
            20                  25                  30

Trp Phe Asp Ile Thr Lys Trp Leu Trp Tyr Ile Lys Ile Phe Ile Met
        35                  40                  45

Ile Val Gly Gly
    50


<210> SEQ ID NO 19
<211> LENGTH: 52
<212> TYPE: PRT
<213> ORGANISM: Human immunodeficiency virus 1

<400> SEQUENCE: 19

Asp Tyr Ile Tyr Ser Leu Leu Glu Asn Ala Gln Asn Gln Gln Glu Lys
1               5                   10                  15
```

```
Asn Glu Gln Glu Leu Leu Glu Leu Asp Lys Trp Ala Ser Leu Trp Asn
            20                  25                  30

Trp Phe Asp Ile Ser Lys Trp Leu Trp Tyr Ile Lys Ile Phe Ile Met
        35                  40                  45

Ile Val Gly Gly
    50


<210> SEQ ID NO 20
<211> LENGTH: 52
<212> TYPE: PRT
<213> ORGANISM: Human immunodeficiency virus 1

<400> SEQUENCE: 20

Gly Phe Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asp Ile Ser Lys Trp Leu Trp Tyr Ile Lys Ile Phe Ile Met
        35                  40                  45

Ile Val Gly Gly
    50


<210> SEQ ID NO 21
<211> LENGTH: 52
<212> TYPE: PRT
<213> ORGANISM: Human immunodeficiency virus 1

<400> SEQUENCE: 21

Asp Phe Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asp Ile Asn Lys Trp Leu Trp Tyr Ile Lys Ile Phe Ile Met
        35                  40                  45

Ile Val Gly Gly
    50


<210> SEQ ID NO 22
<211> LENGTH: 52
<212> TYPE: PRT
<213> ORGANISM: Human immunodeficiency virus 1

<400> SEQUENCE: 22

Asp Phe Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Ser Trp Asn
            20                  25                  30

Trp Phe Asp Ile Asn Lys Trp Leu Trp Tyr Ile Lys Ile Phe Ile Met
        35                  40                  45

Ile Val Gly Gly
    50


<210> SEQ ID NO 23
<211> LENGTH: 52
<212> TYPE: PRT
<213> ORGANISM: Human immunodeficiency virus 1

<400> SEQUENCE: 23

Asp Phe Ile Tyr Ser Leu Leu Glu Asn Ala Gln Asn Gln Gln Glu Lys
1               5                   10                  15
```

-continued

```
Asn Glu Gln Glu Leu Leu Glu Leu Asp Lys Arg Ala Ser Leu Trp Asn
            20                  25                  30

Trp Phe Asp Ile Asn Lys Trp Leu Trp Tyr Ile Lys Ile Phe Ile Met
        35                  40                  45

Ile Val Gly Gly
    50


<210> SEQ ID NO 24
<211> LENGTH: 52
<212> TYPE: PRT
<213> ORGANISM: Human immunodeficiency virus 1

<400> SEQUENCE: 24

Asp Tyr Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asp Ile Asn Lys Trp Leu Trp Tyr Ile Lys Ile Phe Ile Met
        35                  40                  45

Ile Val Gly Gly
    50


<210> SEQ ID NO 25
<211> LENGTH: 52
<212> TYPE: PRT
<213> ORGANISM: Human immunodeficiency virus 1

<400> SEQUENCE: 25

Asp Tyr Ile Tyr Ser Leu Leu Glu Asn Ala Gln Asn Gln Gln Glu Lys
1               5                   10                  15

Asn Glu Gln Glu Leu Leu Gly Leu Asp Lys Trp Ala Ser Leu Trp Asn
            20                  25                  30

Trp Ser Asp Ile Asn Lys Trp Leu Trp Tyr Arg Lys Ile Phe Ile Met
        35                  40                  45

Ile Val Gly Gly
    50


<210> SEQ ID NO 26
<211> LENGTH: 31
<212> TYPE: PRT
<213> ORGANISM: Human immunodeficiency virus 1

<400> SEQUENCE: 26

Gln Gln Glu Lys Asn Glu Gln Glu Leu Leu Glu Leu Asp Lys Trp Ala
1               5                   10                  15

Ser Leu Trp Asn Trp Phe Asn Ile Thr Asn Trp Leu Tyr Ile Lys
            20                  25                  30


<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

tcgtcgttgt cgttttgtcg tt                                           22
```

METHODS FOR THE INDUCTION OF BROADLY ANTI-HIV-1 NEUTRALIZING ANTIBODY RESPONSES EMPLOYING LIPOSOME-MPER PEPTIDE COMPOSITIONS

This application is the U.S. national phase of International Application No. PCT/US2010/001017, filed 5 Apr. 2010, which designated the U.S. and claims the benefit of U.S. Provisional Application No. 61/166,625, filed 3 Apr. 2009, the entire contents of each of which are hereby incorporated by reference.

This invention was made with government support under Grant No. AI 067854 awarded by the National Institutes of Health. The government has certain rights in the invention.

TECHNICAL FIELD

The present invention relates in general, to a formulation suitable for use in inducing anti-HIV-1 antibodies, and, in particular, to a formulation comprising Toll Like Receptor (TLR) agonists with HIV-1 gp41 membrane proximal external region (MPER) peptide-liposome conjugates for induction of broadly reactive anti-HIV-1 antibodies. The invention also relates to methods of inducing neutralizing anti-HIV-1 antibodies using such formulations.

BACKGROUND

One of the major challenges to HIV-1 vaccine development has been the inability of immunogens to induce broadly neutralizing antibodies (nAb). nAbs are generated during HIV-1 infection. However, most of the nAbs generated neutralize only the autologous viruses or closely related strains (Moog et al, J. Virol. 71:3734-3741 (1997), Gray et al, J. Virol. 81:6187-6196 (2007)). HIV envelope (Env) constantly mutates to escape from existing nAb response (Albert et al, Aids 4:107-112 (1990), Wei et al, Nature 422:307-312) (2003)). nAb responses do evolve over the course of the HIV infection. However, with the mutation capacity of HIV-1 viruses, neutralizing antibody responses always seem to “lag behind” virus evolution (Wei et al, Nature 422:307-312 (2003)), Richman et al, Proc. Natl. Acad. Sci. USA 100:4144-4149 (2003), Geffin et al, Virology 310:207-215 (2003)).

After extensive research, a handful of broadly neutralizing monoclonal antibodies (mAbs) against HIV have been identified (Buchacher et al, AIDS Res. Hum. Retroviruses 10:359-369 (1994), Zwick et al, J. Virol. 75:10892-10895 (2001), Burton et al, Proc. Natl. Acad. Sci. USA 888:10134-10137 (1991)). Two such antibodies, 2F5 and 4E10, target the conserved membrane-proximal external region (MPER) of HIV, have a broad spectrum of neutralization (Binley et al, J. Virol. 78:13232-13252 (2004)), and have been shown to neutralize 80% and 100% of newly transmitted viruses (Mehandru et al, J. Virol. 78:14039-14042 (2004)), respectively. When passively administered in combination with several other broadly neutralizing monoclonal antibodies, a cocktail of mAbs composed of 2G12, 2F5 and 4E10 successfully protected the host from virus infection in animal models (Baba et al, Nat. Med. 6:200-206 (2000), Ferrantelli et al, J. Infect. Dis. 189:2167-2173 (2004), Mascola et al, Nat. Med. 6:207-210 (2000), Ruprecht et al, Vaccine 21:3370-3373 (2003)), or delayed virus rebound after cessation of antiretroviral therapy (Trkola et al, Nat. Med. 11:615-622 (2005)).

The potential of using 2F5 and 4E10 to prevent HIV infection is greatly compromised by the fact that HIV infected patients rarely develop these antibodies spontaneously (Dhillon et al, J. Virol. 81:6548-6562 (2007)), and there has been no success in inducing 2F5- and 4E10-like antibodies by vaccination (Kim et al, Vaccine 25:5102-5114 (2006), Coeffier et al, Vaccine 19:684-693 (2000), Joyce et al, J. Biol. Chem. 277:45811-45820 (2002), Ho et al, Vaccine 23:1559-1573 (2005), Zhang et al, Immunobiology 210:639-645 (2005)). Identification of subjects that develop 2F5- or 4E10-like antibodies during natural HIV-1 infection, and developing an understanding of the mechanism of, or hindrance to, these broadly neutralizing antibodies is important for AIDS vaccine design.

The present invention results, at least in part, from the identification and characterization of a rare Env mutation in the HIV-1 MPER region which is associated with an increase in neutralization sensitivity to 2F5 and 4E10 mAbs. The invention also results from the development of constructs that can modulate B cell tolerance and enhance antibody responses against poorly immunogenic HIV-1gp41MPER epitopes.

SUMMARY OF THE INVENTION

In general, the present invention relates to a formulation suitable for use in inducing anti-HIV-1 antibodies. More specifically, the invention relates to a formulation comprising TLR agonists with HIV-1 gp41MPER peptide-liposome conjugates, and to methods of inducing broadly reactive neutralizing anti-HIV-1 antibodies using same.

Objects and advantages of the present invention will be clear from the description that follows.

BRIEF DESCRIPTION OF THE DRAWINGS

FIG. 2 discloses SEQ ID NOS 18-20, 20-22, 22-23, 21, 21-22, 24-25, 25 and 25, respectively, in order of appearance.

FIG. 6A. Comparison of normalized specific binding responses of 2F5 mAb to 2F5 peptide-liposomes (broken line) and L669S mutant peptide-liposomes (solid line). The inset shows the magnified image of the dissociation phase of the 2F5 mAb interaction (120-400 s). FIG. 6B. The encounter-docking model of 2F5 mAb-peptide-liposome interactions and the estimated rate constants of association and dissociation steps.

FIG. 8. HIV-1 gp41 MPER peptides that include the epitopes of the two broadly neutralizing antibodies 2F5 and 4E10. Amino acid sequences of the gp41 MPER peptides (SEQ ID NOS 26, 9-10 and 16-17, respectively, in order of appearance) that can be conjugated to synthetic liposomes are shown.

FIG. 9. Structures of TLR agonists formulated with liposomes. A schematic picture of the immunogen designs shows the peptide-liposomes containing different TLR agonists as adjuvants; TLR4 (Lipid A); TLR9 (oCpG) (SEQ ID NO: 27) and TLR7 (R848).

FIG. 10A shows strong binding of 2F5 mab to gp41 MPER liposome constructs with Lipid A (200 μg dose equivalent). FIG. 10B shows binding of 2F5 mAb to oCpG (50 μg dose equivalent) conjugated gp41 MPER liposomes. FIG. 10C shows binding of 2F5 mAb to R848-conjugated gp41 MPER containing liposomes. In comparison to control liposomes with only TLR adjuvants, strong binding of 2F5 mAb was observed to each of the gp41MPER-adjuvant liposomal constructs.

FIG. 15. Neutralization of QZ4734 and QZ4734/L669S pseudotyped viruses by 2F5 mAb (tested on TZM-b1 cells). QZ4734/L669S was generated by introducing L669S single mutation into the QZ4734 envelope. Numbers by the curves indicate the IC50 values.

FIG. 16. Neutralization of TND_669S and two other stains (7534.2 and 7534.11) isolated from the same plasma sample (15 mo post infection) by 2F5 and TriMab (1:1:1 combination of 2F5, 4E10 and 2G12). Numbers above each bar represents IC50 values. The test was performed on TZM-b1 cells.

DETAILED DESCRIPTION OF THE INVENTION

Figure 1:
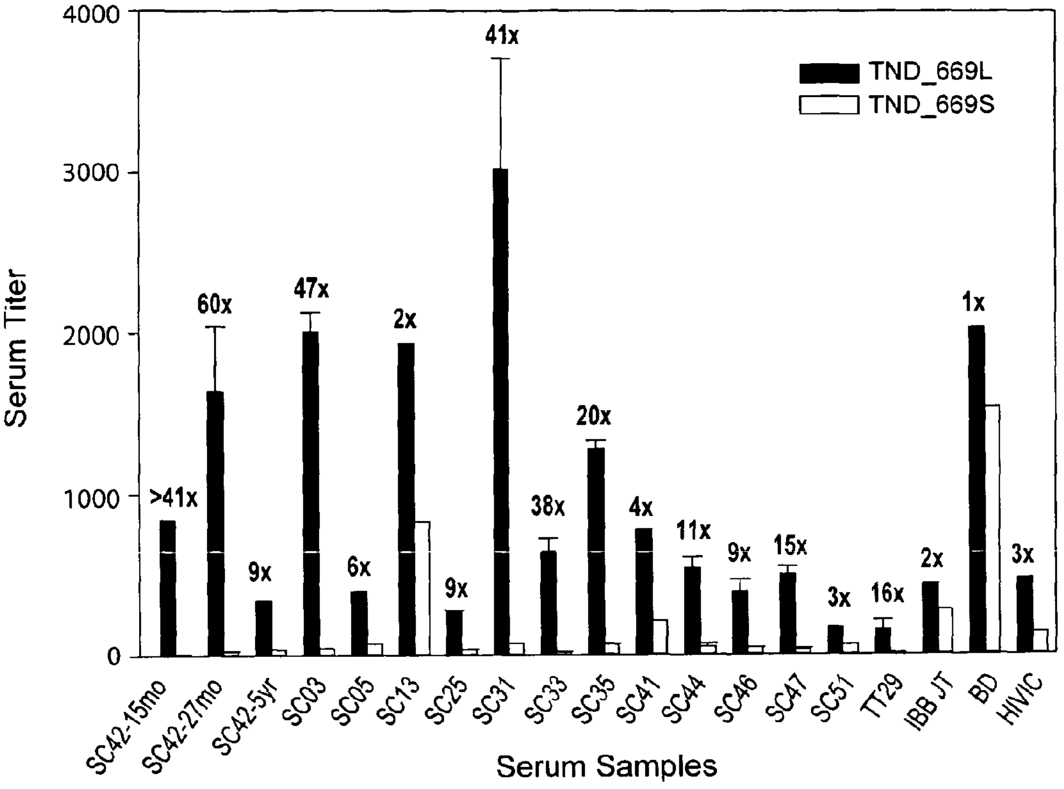
FIG. 1. Neutralizing sensitivity of TND_669S and TND_669L Env-pseudoviruses by autologous and heterologous sera/Ab. SC42-15mo, SC42-27mo, and SC42-5yr are autologous sera from 15mo, 27mo, and 65 mo p.i.; SCO3-TT29 are heterologous sera from Trinidad cohort; IBBJT, BD are HIV+ patient sera used as positive controls; HIVIG is purified pooled IgG from HIV+ patient sera. Due to sample availability limitation, not all samples were tested more than once. For those samples that were tested more than once, the bars represents the average titer, and the error bars represent standard errors.

The present invention relates to a liposome-based adjuvant conjugate that presents TLR ligands and HIV-1 gp41 neutralizing antigens, and to a method of inducing neutralizing anti-HIV-1 antibodies in a subject (e.g., a human subject) using same. Suitable neutralizing antigens include gp41MPER epitope peptides (Armbruster et al, J. Antimicrob. Chemother. 54:915-920 (2004), Stiegler and Katinger, J. Antimicrob. Chemother. 512:757-759 (2003), Zwick et al, Journal of Virology 79:1252-1261 (2005), Purtscher et al, AIDS10:587 (1996)) and variants thereof, for example, variants that confer higher neutralization sensitivity to MPER Mabs 2F5 and 4E10. In a preferred embodiment, the variant is a MPER epitope peptide with an L669S mutation that confers higher neutralization sensitivity to MPER mAbs 2F5 and 4E10 (Shen et al, J. Virology 83: 3617-25 (2009)).

Liposomes suitable for use in the invention include, but are not limited to, those comprising POPC, POPE, DMPA (or sphingomyelin (SM)), lysophosphorylcholine, phosphatidylserine, and cholesterol (Ch). While optimum ratios can be determined by one skilled in the art, examples include POPC: POPE (or POPS):SM:Ch or POPC:POPE (or POPS):DMPA: Ch at ratios of 45:25:20:10. Alternative formulations of liposomes that can be used include DMPC (1,2-dimyristoyl-sn-glycero-3-phosphocholine) (or lysophosphorylcholine), cholesterol (Ch) and DMPG (1,2-dimyristoyl-sn-glycero-3-phoshpho-rac-(1-glycerol) formulated at a molar ratio of 9:7.5:1 (Wassef et al, ImmunoMethods 4:217-222 (1994); Alving et al, G. Gregoriadis (ed.), Liposome technology $2^{nd}$ ed., vol. III CRC Press, Inc., Boca Raton, Fla. (1993); Richards et al, Infect. Immun. 66(6):285902865 (1998)). The above-described lipid compositions can be complexed with lipid A and used as an immunogen to induce antibody responses against phospholipids (Schuster et al, J. Immunol. 122:900-905 (1979)). A preferred formulation comprises POPC:POPS:Ch at ratios of 60:30:10 complexed with lipid A according to Schuster et al, J. Immunol. 122:900-905 (1979).

In accordance with the invention, immune response enhancing TLR ligands, for example, monophosphorylipid A (MPL-A, TLR4 ligand), oligo CpG (TLR9 ligand) and R-848 (TLR7/8 ligand), are formulated either individually or in combination into liposomes conjugated with an HIV-1 gp41MPER peptide immunogen. A preferred combination of TLR agonists comprises oCpG (TLR9) (Hemni et al, Nature 408:740-745 (2004)) and R848 (TLR7/8) (Hemni et al, Nat. Immunol. 3:196-200 (2002)).

Additional designs of constructs of the invention include MPER peptide-liposome encapsulated with the cytokine interferon (IFN)-α and either encapsulated or membrane bound CD40 ligand. Two broadly neutralizing gp41 MPER antibodies (2F5, 4E10) bind with high affinity to such TLR ligand adjuvant-associated liposome constructs. These constructs can be used to modulate B cell tolerance, direct liposomes to certain B cell populations capable of making broadly reactive neutralizing antibodies, and in enhance antibody responses against poorly immunogenic HIV-1 gp41MPER epitopes.

Autoreactive B cells can be activated by TLR ligands through a mechanism dependent on dual engagement of the B cell receptor (BCR) and TLR (Leadbetter et al, Nature 416: 603 (2002); Marshak-Rothstein et al, Annu. Rev. Immunol. 25: 419-41 (2007), Herlands et al, Immunity 29:249-260 (2008), Schlomchik, Immunity 28:18-28 (2008)). In a preferred immunogen design of the instant invention, soluble IFN-α is encapsulated into liposomes conjugated to MPER peptides such as MPER656 or MPER656-L669S peptides. IFN-α has been reported to modulate and relax the selectivity for autoreactive B cells by lowering the BCR activation threshold (Uccellini et al, J. Immunol. 181:5875-5884 (2008)). The design of the immunogens results from the observation that lipid reactivity of gp41MPER antibodies is required for both binding to membrane bound MPER epitopes and in the neutralization of HIV-1.

The B cell subsets that the liposomes can target include any B cell subset capable of making polyreactive antibodies that react with both lipids and the gp41 epitopes of the MPER. These B cell subsets include, but are not limited to, the marginal zone IgM+ CD27+ B cell subset (Weill et al, Annu. Rev. Immunol. 27:267-85 (2009), Li et al, J. Exp. Med 195: 181-188 (2002)), the transitional populations of human B cells (Sims et al, Blood 105:4390-4398 (2005)), and the human equivalent of the B cells that express the human equivalent of the mouse Immunoglobulin (Ig) light chain lambda X (Li et al, Proc. Natl. Acad. Sci. 103:11264-11269 (2006), Witsch et al, J. Exp. Med. 203:1761-1772 (2006)). All of these B cell subsets have the capacity to make multireactive antibodies and, therefore, to make antibodies that have the characteristic of reacting with both lipids and HIV-1 gp41. That the liposomes have the characteristic of having both lipids and gp41 in them, should result in the selective targeting of these immunogens to the B cells of interest. Because these liposomes can be used to transiently break tolerance of B cells or to target rare B cell subsets, it can be seen that other HIV-1 envelope immunogens, such as deglycosylated envelope preparations, such as described below, can be formulated in the liposomes containing TLR4 agonists, TLR7/8 agonists and IFN α.

The deglycosylated JRFL gp 140 Env protein and the CD4-binding site mutant gp140 (JRFL APA) have been described in a previous application (see, for example, WO 2008/033500). Deglycosylated env and Env mutated to not bind CD4 so as not to be immunosuppressive can be anchored in the liposomes by incorporating a transmembrane domain and, after solubilizing in detergent, can be reconstituted into synthetic lipsomes. Alternatively, His-tagged (c-terminus end) versions of the Env gp140 can be anchored into liposomes as described for an intermediate form of HIV-1 gp41 (gp41-inter)

Given that many B cell subsets capable of making polyreactive antibodies also bind mammalian DNA, addition of DNA to liposomes can be used to target the immunogens to the responsive B cells.

The liposome-containing formulations of the invention can be administered, for example, by intramuscular, intravenous, intraperitoneal or subcutaneous injection. Additionally, the formulations can be administered via the intranasal route, or intrarectally or vaginally as a suppository-like vehicle. Generally, the liposomes are suspended in an aqueous liquid such as normal saline or phosphate buffered saline pH 7.0. Optimum dosing regimens can be readily determined by one skilled in the art.

Certain aspects of the invention can be described in greater detail in the non-limiting Examples that follows. See also Published PCT Application Nos. WO 2006/110831 and WO 2008/127651, U.S. Published Application Nos. 2008/0031890 and 2008/0057075, U.S. Provisional Application No. 60/960,413 and U.S. application Ser. No. 11/918,219. (See also related applications entitled “Formulation”, filed Apr. 3, 2009 and “Mouse Model”, filed Apr. 3, 2009 .

EXAMPLE 1

Experimental Details

Subjects

Trinidad Seroconverter Cohort was described preciously (Blattner et al, J. Infect. Dis. 189:1793-1801 (2004)). Briefly, patients from a sexually transmitted disease (STD) clinic were monitored for HIV infection and enrolled upon seroconvertion. Infections occurred through heterosexual contact and subtype B viruses accounted for all the infections. The patient of interest in this study, SC42, was naïve for antiviral therapy until 5 yr into infection.

Molecular Cloning of Full-Length Envelopes

Cloning strategy of full-length gp160 has been described previously (Wei et al, Nature 422:307-312 (2003), Li et al, J. Virol. 79:10108-10125 (2005)). Briefly, viral RNA was extracted from patient plasma samples using QIAmp Viral RNA Mini Kit (Qiagen, Valencia, CA) and subsequently reverse-transcribed into cDNA using SuperScript II ((Invitrogen Corp., Carlsbad, CA) and random hexamer primers. Full length envelope sequences were generated by nested PCR with the following primers: 1st round primers 5'OUT 5'-TAGAGCCCTGGAAGCATCCAGGAAG- 3'(SEQ ID NO: 1), nt 5852-5876 and 3'OUT 5'-TTGCTACTTGTGATTGCTCCATGT-3'(SEQ ID NO: 2), nt 8912-8935); and 2nd round primers 5'Intopo 5'-CACCTAGGCATCTCCTATGGCAGGAAGA AG-3'(SEQ ID NO: 3), nt 5957-5982and 3'IN 5'-GTCTCGAGATACTGCTCCCACCC-3'(SEQ ID NO: 4), nt 8881-8903). The PCR products were purified and then directly ligated into the directional cloning vector pcDNA 3.1 D/V5-His-TOPO (Invitrogen) following the manufacturer's directions. This pcDNA 3.1 D/V5- His-TOPO vector contains a cytomegalovirus promoter that allows the expression of envelope proteins for subsequent pseudovirus production.

Mutagenesis for Introduction of Single Mutation

A QuikChange XL Site-directed Mutagenesis Kit (Invitrogen Corp) was used to introduce S669L mutation into HS-MPER to generate HS-MPERIS669L, and K665N mutation into HS-MPER to generate HS-MPER/K665N following the manufactures instructions. The primers for introducing S669L mutation into HS-MPER were: fN-MPER_S669L (5'-ggataagtgggcaagtttgtggaattggtttgac-3'(SEQ ID NO: 5)) and r7534.5_S669L (5'-GTCAAACCAATTCCACAAACTTGCCCACTTATCC3'(SEQ ID NO: 6)); the primers for introducing K665N into HS-MPER were: fHS-MPER_K665N (5'-gaattattagaattggataaCtgggcaagttcgtgg3' (SEQ ID NO: 7)) and r7534.5_K665N (5'-CCACGAACTTGCCCAGTTATCCAATTCTAATAATTC3'(SEQ ID NO: 8)).

Production and Titration of Env-Pseudoviruses

Production and titration of the env-pseudoviruses was conducted following procedures modified from methods previously described (Li et al, J. Virol. 79:10108-10125 (2005)) with minor modifications. Full-length env clones in pcDNA3.1D/V5-His-TOPO vector were co-transfected into 293T cells with an env-deficient HIV-1 backbone (pSG3Δenv) using FuGENE® HD transfection reagent (Roche Applied Science, Basel, Switzerland). Tissue culture fluid was harvested after 24-36 h of incubation and fresh fetal bovine serum was added to the virus stock to make a final concentration of 20%.

The 50% tissue culture infectious dose (TCID50) of each virus preparation was determined on JC53-BL cells as previously described (Li et al, J. Virol. 79:10108-10125 (2005)). Briefly, serial diluted virus stocks were used to infect JC53-BL cells on 96-well-flat-bottom-plates for 48 h. The cells were then lysed with and the relative luminescence units (RLU) determined by BriteLite™ assay system (PerkinElmer, Inc., Waltham, Mass.). Wells with luciferase luminescence 2.5-fold over that of the cells only control were considered positive for virus infection. TCID50 was calculated using the Reed-Muench formula.

Neutralization Assay

Neutralization assays for the pseudoviruses were performed on JC53-BL cells on 96-well-flat-bottom-plates as previously described (Li et al, J. Virol. 79:10108-10125 (2005)). Briefly, serially diluted serum samples or purified Abs were incubated with testing viruses, followed by addition of JC53-BL cells. The relative luminescence unit (RLU) of each well was measured with BriteLite™ assay system and the IC50 was determined as the highest dilution of serum (in cases of serum samples) or the lowest concentration of Ab (in cases of purified Abs) that was able to inhibit virus infection by 50% compared to the virus control.

Peptide Absorption Neutralization Assay

Peptide absorption neutralization assay was modified from neutralization assay. Serially diluted serum samples or purified Abs were pre-incubated with properly diluted peptide for 1 h before addition of virus, followed by regular neutralization assays.

Surface Plasmon Resonance (SPR) Assays

SPR binding assays were performed on a BIAcore 3000 (BIAcore Inc, Piscattaway, NJ) maintained at 20° C. as previously described (Alam et al, J. Immunol. 178:4424-4435 (2007)). Biotinylated versions of SP62 peptides- gp41 652-671 (QQEKNEQELLELDKWASLWN (SEQ ID NO: 9)) and SP62-L669S (gp41 652-671) (QQEKNEQELLELDKWASSWN (SEQ ID NO: 10)), and control peptides with scrambled sequences (2F5$_{656-670}$ Scrambled and 2F5$_{656-670/L669S}$Scrambled), were individually anchored on a BIAcore SA sensor chip as described (Alam et al, J. Immunol. 178: 4424-4435 (2007), Alam et al, AIDS Res. Hum. Retroviruses 20:836-845(2004)). Each peptide was injected until 100 to 150 response unit (RU) of binding to streptavidin was observed. Specific binding responses of mAb binding were obtained following subtraction of non-specific binding on the scrambled 2F5 peptide surface. Rate constants were measured using the bivalent analyte model (to account for the avidity of bivalent Ig molecules) and global curve fitting to binding curves obtained from 2F5 titrations, which ranged from 0.01to 119 nM for mAb 2F5.mAb 2F5 were injected at 30 uL/min for 2-6 min and Glycine-HCl pH 2.0and surfactant P20 (0.01%) were used as the regeneration buffer.

SPR assay with liposome-anchored peptides were done in a similar fashion as described above. The peptides used are SP62 (gp41 652-671)-GTH1 (QQEKNEQELLELDKWASLWNYKRWIILGLNKIVRMYS-biotin, containing the consensus 2F5 epitope (SEQ ID NO: 11)) and SP62-L669S (gp41 652-671)-GTH1 (QQEKNEQELLELDKWASSWNYKRWIILGLNKIVRMYS-biotin, containing the 2F5 epitope with the L669S substitution (SEQ ID NO: 12)).

Fitness Assay

The dual infection fitness assay was performed as previously described (Lu et al, J. Virol. 78:4628-4637 (2004)) with minor modifications. HIV-1 infectious chimeric viruses containing TND_669S or TND_669L env and a marker sequence (either *Salmonella enterica* serovar *Typhimurium* histidinol dehydrogenase [hisD] gene or the human placental heat-stable alkaline phosphatase [PLAP] gene) were generated by cotranfecting env PCR product and NL4-3 background vector with a reporter gene. In a dual infection fitness assay, two chimeric viruses with specific input ratio (as determined by real-time PCR of the reporter genes) were used to co-infect PBMC (MOI=0.001). Relative production of the viruses with the two Env species in the culture were measured by the corresponding marker (hisD or PLAP) using real-time RT-PCR. Production of an individual virus in a dual infection was determined by calculating the percentage of the individual virus in the total virus population at specific time points (Day 4, 7, and 10). The relative fitness value (1+S) of the individual virus was determined by following equation as previously described (Wu et al, J. Virol. 80:2380-2389 (2006)):

$$(1+S=\exp(d)=\exp\{\ln[(TM(t2) \times TL(t1))/(TL(t2) \times TM(t1))]/\Delta t\}$$

1+S=exp, where S is the selection coefficient; $M_t$, $M_0$, $L_t$, and $L_0$ are the proportion of more fit variant or less fit variant at time point t and the initial proportion (0) in the inoculum respectively.

Results

Identification of TND_669S Envelope

Multiple longitudinal Env clones were obtained from plasma samples of SC42, NL4-3 Env-pseudotyped viruses were made from the Env clones, and neutralizing sensitivity of selected Env clones against autologous as well as heterologous sera was tested. An envelope strain that was highly sensitive to neutralization by autologous sera was identified. TND_669S, an envelope clone obtained from a chronically infected HIV+ subject showed unexpectedly high sensitivity to neutralization by both autologous and heterologous sera. TND_669S was neutralized by contemporaneous and 27 month (post enrollment) autologous sera with titers of 845 and 1,353 respectively, while TND_669L, another isolate the neutralization sensitivity of which was typical of envelope clones obtained from the same time point (15 month post enrollment) and was retrospectively selected for comparison based on its envelope sequence, was not sensitive to contemporaneous autologous serum neutralization and was neutralized by 27 months post enrollment autologous serum with a titer of only 26 (FIG. 1). TND_669S and TND_669L Env-pseudoviruses were then tested against a panel heterologous patient sera as well as several HIV+ sera/Ab used as positive controls. TND_669S Env-pseudovirus was shown to be up to 47-fold more sensitive to neutralization by heterologous sera within Trinidad cohort. Among the 14 patient sera tested, 7 neutralized the TND_669S pseudovirus more than 10-fold more efficiently than the TND_669L pseudovirus (FIG. 1).

Identification of the L669S Mutation

Figure 2:
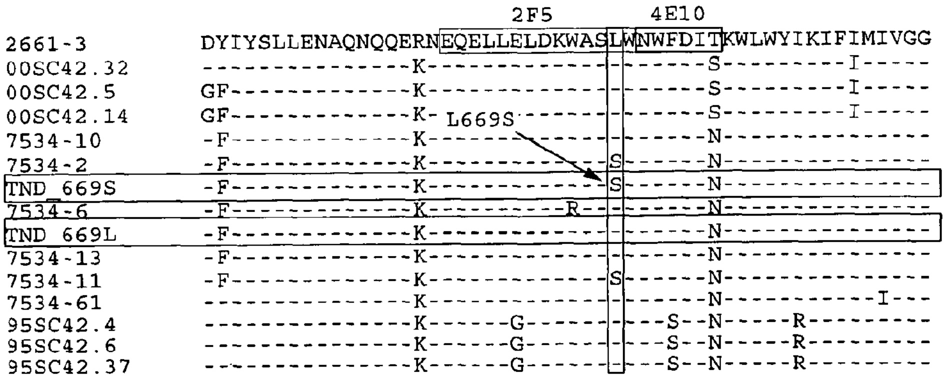
FIG. 2. Partial alignment of selected SC42 Env sequences. TND_669S, TND_669L and 7534-xx (wherein “xx” is as shown in FIG. 2) are sequences from 15 mo p.i. plasma; Other sequence shown are selected sequences from week 0 (2661-x), week 1 (00SC42-xx) and from 60 mo (95SC42-xx) (wherein “x” and “xx” are as shown in FIG. 2) p.i. plasma. Consensus epitope sequences for 2F5 and 4E10 are highlighted in blue and green boxes, respectively.

The protein and DNA sequences for TND_669S and TND_669L gp 160 were examined for genetic variations responsible for the increased neutralizing sensitivity of TND_669S envelope. There are 6 nucleotide differences between the two env DNA sequences. However, 5 of those are synomonous mutations, resulting in a single amino acid difference between TND_669S and TND_669L Env. The single amino acid difference is located at position 669, near the C-terminus of the 2F5 epitope and 2 aa upstream of the 4E10 epitope in the MPER (FIG. 2). TND_669L contains the 2F5 consensus sequence while TND_669S contains a L669S mutation. 3 out of 10 clones obtained from the 15 month post enrollment plasma of patient SC42 contain this mutation, while this mutation was not found in either 1 wk post enrollment plasma or 5 yr post enrollment plasma. Interestingly, only 1 out of around 1000 full-length Env sequences in LANL database contains this L669S mutation.

Sensitivity of the L669s Mutant to Monoclonal Antibodies

Figures 3A, 3B:
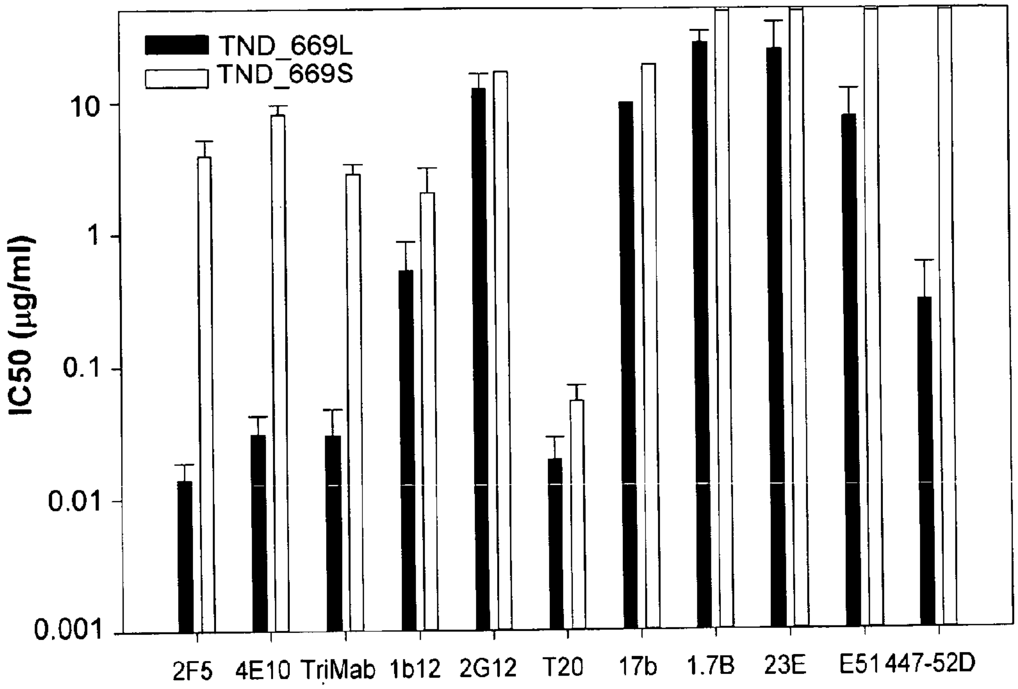
FIGS. 3A and 3B. Neutralization of TND_669S and TND_669L Env-pseudoviruses by various monoclonal antibodies and the entry inhibitor T20. The mean IC50 of each reagent against the two strains are shown in FIG. 3A, with error bars showing the standard errors. The IC50 values and the fold differences of each neutralizing antibodies in its potency against TND_669S and TND_669L are shown in FIG. 3B. Each IC50 was obtained from at least two independent tests. Data for 2F5, 4E10, TriMab, 1b12, and 2G12 also include one set of data from a test performed by Dr. Montefiori’s laboratory (Duke University). The fold difference between the IC50 of each mAb against TND_669S and TND_669L (TND_669:tND_669L) are listed in the last column of the table, and the ones with significant increase in sensitivity of TND_669S are highlighted in yellow (and marked with a "√").

Based on the location of the L669S mutation, sensitivity of the TND_669S and TND_669L to 2F5 and 4E10 mAbs was tested. Not surprisingly, TND_669S was highly sensitive to 2F5 mAb while TND_669L was only moderately sensitive (FIG. 3). Interestingly, TND_669S is also highly sensitive to neutralization by 4E10 mAb compared to TND_669L. As shown in FIG. 3, the $IC_{50}$ of 2F5 and 4E10 mAbs against TND_669S Env-pseudovirus were 279- and 275-fold lower than that against TND_669L Env-pseudovirus, respectively. The mean $IC_{50}$ of TND_669S and TND_669L were 0.014 (±0.0056) and 3.92 (±~1.52) respectivelym for 2F5, and 0.031 (±0.012) and 8.49 (±1.29) μg/ml, respectively, for 4E10.

Sensitivity of TND_669S and TND_669L pseudoviruses to several other neutralizing agents, including the glycan dependent mAb 52D and the entry inhibitor T20 was also tested (FIG. 3). No significant difference in sensitivity to 2G12 and T20 and only a slight increase in sensitivity to 17b and 1b12 (−2 and 4-fold, respectively) was observed for the TND_669S pseudovirus, indicating that global changes in envelope, if any, can not account for the dramatically enhanced neutralizing sensitivity observed for the TND_669S envelope. Differences in sensitivity of the two strains against 1.7B, 23E, and E51 could not be quantified because the TND_669L is not sensitive enough to neutralization by these antibodies. Interestingly, the TND_669L envelope was also not sensitive to 447-52D neutralization while the TND_669L envelope was neutralized with an $IC_{50}$ of 0.31 μg/ml, indicating an enhancement of >161-fold in 447-52D sensitivity associated with the L669S mutation.

Single L669S Mutation Accounts for the Phenotypic Change

To confirm that the L669S mutation alone is responsible for the phenotypic change, a S669L mutation was introduced into the TND_669S envelope by site-directed mutagenesis. The resulting TND_669S/S669L showed only moderate sensitivity to 2F5 comparable to that of TND_669L, confirming the sole contribution of the L669S mutation in the TND 669S to the increased sensitivity to neutralization. Next, the role of the virus backbone in the phenotypic change associated with the L669S mutation was investigated. A L669S mutation was introduced into the envelope of another primary isolate, QZ4734. The L669S mutation rendered the QZ4734 Env-pseudovirus more than two logarithmic magnitudes more sensitive to neutralization by the 2F5 mAb (FIG. 15). Furthermore, the other two clones that share the L669S mutation showed similar magnitude of increase in sensitivity against 2F5 (FIG. 16). These findings suggest that the L669S can increase the sensitivity of HIV-1 envelope to neutralization by MPER antibodies regardless of the virus background.

Neutralizing of TND_669S Envelope is Mediated by 2F5 Binding to its Conventional Epitope Characterization of a 2F5-resistent Env variant has shown that a K665N mutation in the DKW core region abrogates 2F5 binding and results in 2F5 resistance (Purtscher et al, Aids 10:587-593 (1996)). This suggests that the DKW in the core region of the 2F5 epitope EQELLELDKWASLWN (SEQ ID NO: 13) is essential for 2F5 binding. To test whether the potent neutralization of the TND_669S envelope by 2F5 is also mediated though binding of the 2F5 mAb to the core amino acids of the conventional 2F5 epitope, a TND_669S/K665N mutant was made and its sensitivity to 2F5 and 4E10 mAbs was tested. Introduction of the K665N mutation into the TND_669S envelope resulted in a fully 2F5-resistent phenotype while the sensitivity of the envelope against 4E10 was not affected.

Ability of the 2F5 Peptides to Absorb the Neutralizing Activity of the 2F5 mAb

Figures 4A, 4B:
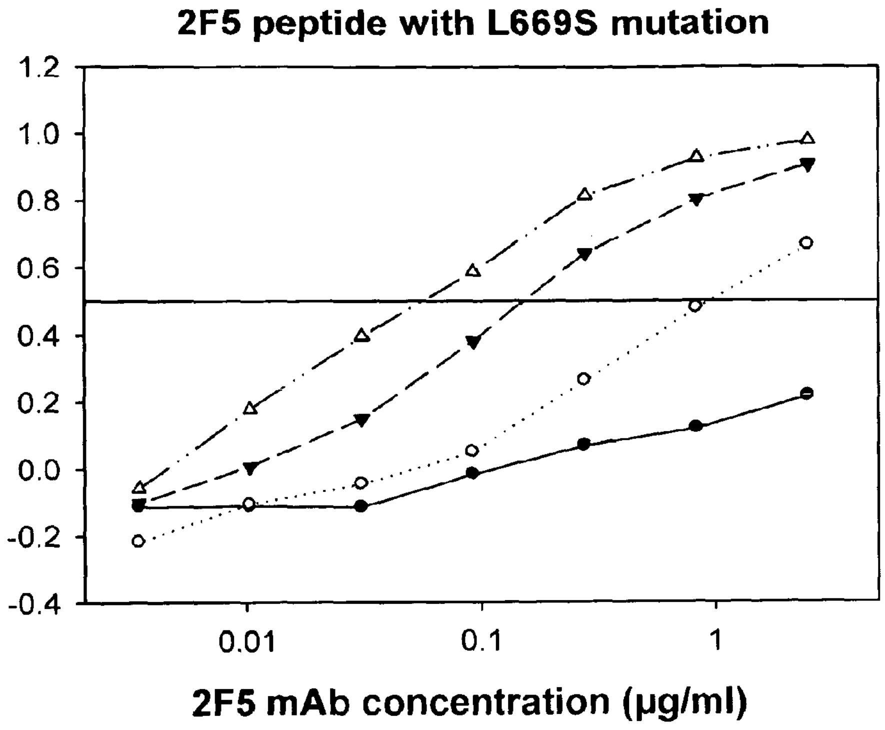
FIGS. 4A and 4B. Peptide absorption neutralization assays. Neutralization of the TND_669S Env-pseudovirus by mAb 2F5 was tested with different doses of 2F5 peptides. Inhibition of 2F5 mAb neutralization by the mutant peptide (containing 2F5 epitope with the L669S mutation, $2F5_{656-670}$/L669S) is shown FIG. 4A. The inhibition curves generated by the peptide containing the consensus peptide (consensus peptide) are similar. The IC50 data are summarized in the table in FIG. 4 B. Similar tests were also performed on the TND_669L viruses. A similar trend was observed, however, due to the low sensitivity of TND_669L to 2F5 mAb, data generated using the TND_669L pseudovirus were not quantitative.
Figures 6A, 6B:
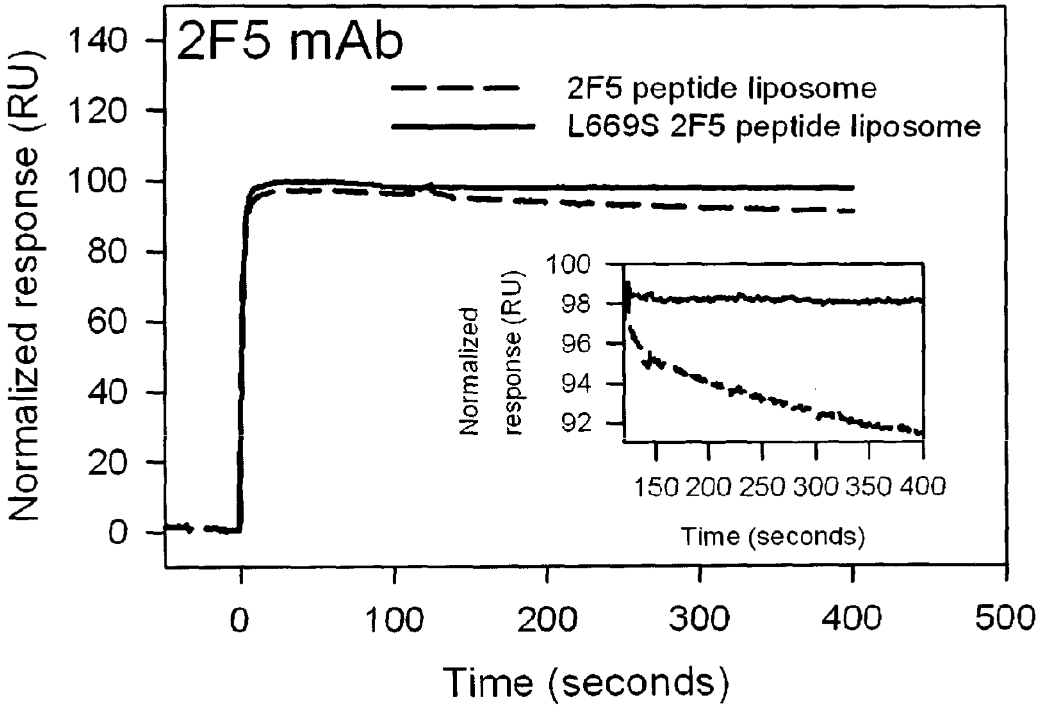
FIGS. 6A and 6B. Binding of 2F5 mAb to peptide-liposome conjugates.

To investigate the possible mechanisms involved in the ability of the L669S substitution to increase the MPER neutralizing sensitivity, peptides containing either the consensus 2F5 epitope ($2F5_{656-670}$) or the 2F5 epitope with the L669S substitution ($2F5_{656-670/L669S}$) were synthesized and subsequently tested for their ability to absorb 2F5 mAb neutralizing activity. The 2F5 mAb was pre-absorbed with either the F5con or the F5mut peptide prior to the neutralization assay. Surprisingly, F5mut did not inhibit 2F5 mAb neutralization more potently than F5con. As show in FIGS. 6A and 6B, both peptides inhibited 2F5 neutralization of the TND_669S Env pseudovirus in a dose-dependent manner. However, F5con is more efficient at inhibiting 2F5 neutralization, manifested by comparable levels of inhibition achieved by 3 μM of F5mut (reduced the $IC_{50}$ of the 2F5 mAb to 0.951 μg/ml) and 0.3 μM of F5con (reduced the $IC_{50}$ of the 2F5 mAb to 0.911 μg/ml) (FIG. 4B).

Figure 5B:
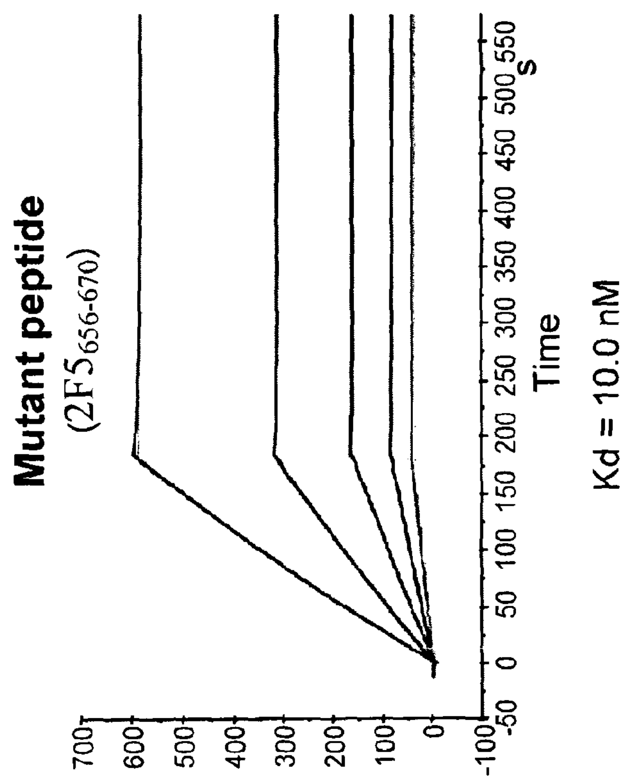
FIGS. 5A and 5B. BIAcore SPR assay for binding avidity of F5mut (FIG. 5A) and F5con (FIG. 5B) peptides to mAb 2F5.
Figure 5A:
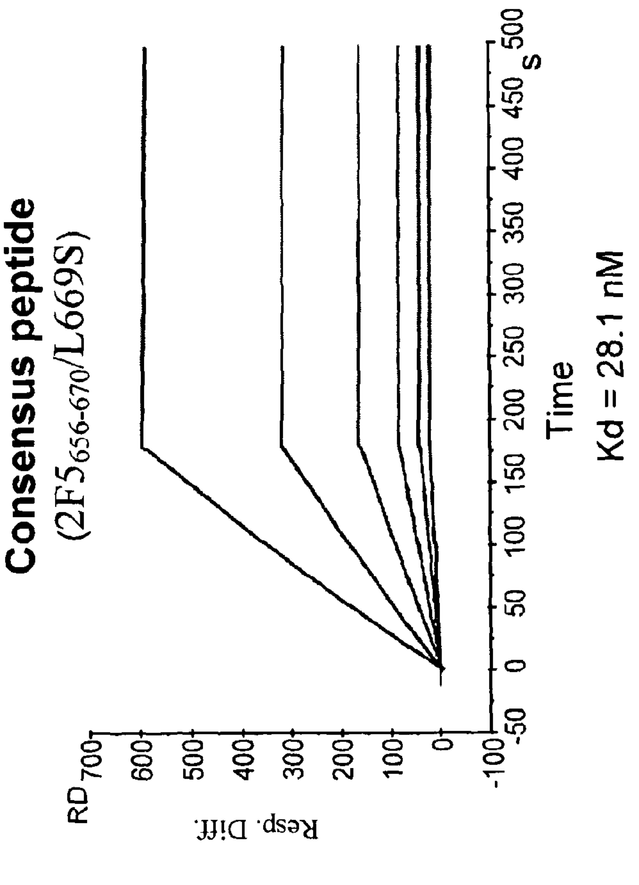

L669S Mutation Did not Increase the Binding Avidity of the 2F5 mAb for its Epitope To investigate the possibility that the L669S mutation enhances the avidity of the 2F5 epitope to the 2F5 mAb, peptides containing either the consensus 2F5 epitope ($2F5_{656-670}$) or the 2F5 epitope with the L669S mutation ($2F5_{656-670/L669S}$), along with the scrambled version for each peptide, were tested in a BIAcore SPR (surface plasmon resonance) assay for 2F5-binding thermodynamics. The equilibrium dissociation constants (KD) for the F5con and F5mut peptides were 11.0 and 28.1 nM, respectively (FIG. 5), indicating that F5con binds to 2F5 with a slightly higher avidity than that of F5mut, although this 2.7-fold difference is not significantly different. Binding ELISA data also confirmed that there was no significant difference between the binding of the two peptides by 2F5 mAb (FIG. 5). This suggests that other factors may be involved in the differential sensitivity of the MPER sequences such as a conformational change in the MPER that alters the exposure of this region to neutralizing antibodies.

Binding of the Peptides to 2F5 mAb in Lipid Environment

In HIV-1 virus, MPER is in close proximity to the envelope lipid bilayer. Direct binding SPR assay has shown that 2F5 mAb binds to F5con and F5con peptides with comparable avidity. To further examine the possible influence of the L669S substitution on binding of the 2F5 mAb to its epitope in a lipid environment, a SPR binding assay was performed using peptides anchored to phospholipid-containing liposomes. As shown in FIG. 6, the peptide containing the L669S substitution bound 2F5 mAb with a response unit of 616.7 (background subtracted) at 10 seconds after the injection was stopped, while the consensus 2F5 epitope bound 2F5 with a response unit of 494.6, indicating that in a lipid environment, a 2F5 peptide with the L669S substitution does bind stronger to 2F5 mAb than the consensus 2F5 mAb.

Fitness of TND_669S Virus is Greatly Impaired

Figure 7:
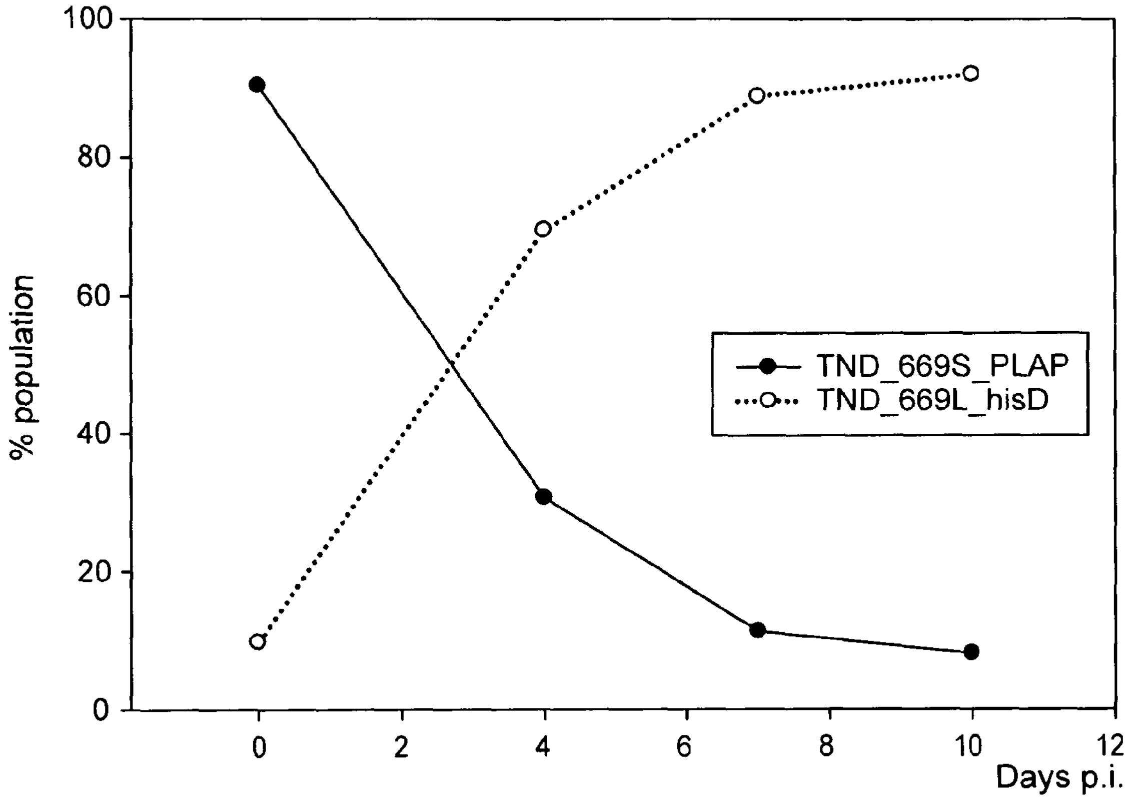
FIG. 7. Dual infection fitness assay in PBMC. Shown is a test with input ratio of 9:1 (TND_669S:TND_669L). The relative fitness value 1+S=1.86. (1+S=exp(d)=exp{ ln [(TM (t2)×TL(t1))/(TL(t2)×TM(t1))]/Δt}. Tests of 3 individual tests with different virus input ratios all conferred a 1+S value of 1.80~1.90.

To determine if the alteration in MPER structure resulted in a fitness defect, the relative fitness of TND_669S and TND_669L viruses was examined by a dual infection competition assay in peripheral blood lymphocytes, using replication competent recombinant viruses containing the NL4-3 backbone and the TND_669S and TND_669L envelope sequences, respectively. With an input ratio of 9:1 (TND_669S:TND_669L), the TND_669S virus was outgrown by the TND_669L virus at 4 days post infection (FIG. 7), suggesting a significant loss of fitness associated with the L669S mutation in the TND 669S virus. The calculated relative fitness (1+S) is 1.86. To further quantify the fitness differences, a ratio of 1:4 (TND_669S:TND_669L) was also examined and confirmed the lowered fitness of the TND 669S virus (data not shown).

In summary, a mutation in the HIV-1 envelope, L669S, has been identified that significantly increases the neutralization sensitivity of the envelope to both 2F5 and 4E10 mAb neutralization. The mean $IC_{50}$ of the TND_669S and TND_669L Env-pseudoviruses against mAbs 2F5 and 4E10 are 0.014 and 0.031 μg/ml, respectively. In a study by Binley et al (J. Virol. 78:13232-13252 (2004)), where a panel of 93 HIV-1 strains were examined for neutralizing sensitivity to various mAbs, most isolates were neutralized by 2F5 and 4E10 with $IC_{50}$ of 1-10 μg/ml, while only 9 strains were neutralized at $IC_{50}$<1 μg/ml by 2F5 mAb, and 9 neutralized by 4E10 mAb at $IC_{50}$ of <1.0 μg/ml. The $IC_{50}$ of TND_669S against 2F5 and 4E10 mAbs was even lower than the most 2F5/4E10 mAb sensitive strain (BUSxxxMNc), which was neutralized by 2F5 and 4E10 mAb with $IC_{50}$ values of 0.05 and 0.17 μg/ml, respectively. In comparison, the L669S mutation renders the envelope 4- and 5-fold more sensitive to 2F5 and 4E10 mAb neutralization, respectively, than the most sensitive virus previously reported.

A single amino acid mutation L669S is responsible for this specific phenotype, as supported by site directed mutagenesis of the L669S mutation into another primary isolate, QZ4734, which rendered the QZ4734/L669S Env-pseudovirus more than 2 logs more sensitive to 2F5 mAb neutralization. To further confirm this, the serine at position 669 of the TND_669S was also mutated back to leucine resulting in the loss of the ultra sensitivity observed in TND_669S envelope.

Both TND_669S and TND 669L envelopes were obtained through bulk PCR. Single genome amplification (SGA) was performed later but the envelope sequences were not identified indicating that the L669S mutation was not circulating in vivo. Additionally, the L669S mutation results in a significant loss of fitness indicating that even if present in natural infection, it would not have circulated long because of its poor fitness level.

In an elegant alkaline-scanning mutagenesis study by Zwick et al, J. Virol. 79:1252-1261 (2005), 13 out of 21 MPER Ala mutants were more sensitive to 2F5 or 4E10 mAb, or both, than the parental MPER. An L669A mutation in HIV-1 JR2 was 50- and 45-fold more sensitive to neutralization by 2F5 and 4E10 mAbs, respectively, and was among the most sensitivity-enhancing mutations. These findings, together with present data, suggest that there may be some common mechanisms shared by the 2F5 and 4E10 epitopes, such as the structure or the accessibility of the MPER, that greatly affects Env sensitivity to MPER neutralizing antibodies.

The mechanisms of the L669S substitution-associated increase in HIV-1 envelope sensitivity to MPER neutralization warrants in depth study because it sheds light on the neutralizing mechanisms of 2F5 and 4E10, and provides important information regarding immunogen design to elicit these types of antibodies.

There are multiple ways through which this mutation may increase neutralizing sensitivity. First, the mutation could have caused dramatic changes in Env and affected the expression level of functional Env spikes on viral particles. Neutralizing assays with multiple other neutralizing agents showed that the increase in neutralizing sensitivity of the TND_669S envelope is not a global effect, making it unlikely that L669S mutation enhances neutralizing sensitivity through changes in Env expression levels. Secondly, this mutation could have changed the fusion kinetics of gp41, resulting in a slower fusion process. Env with reduced fusion kinetics have been shown to be more sensitive to 2F5 and 4E10 neutralization (Reeves et al, J. Virol. 79:4991-4999 (2005)). This is unlikely since the sensitivity of the TND_669S envelope to T20 was only 3-fold that of the TND_669L envelope, suggesting the fusion kinetics is not changed considerably by L669S mutation. Thirdly, it is possible that the L669S mutation itself renders higher avidity binding of the 2F5 mAb to the 2F5 epitope. This hypothesis, however, is not supported by the surface plasmon resonance (SPR) assay results for peptide binding to 2F5, where the 2F5 consensus peptide (containing the consensus 2F5 epitope sequence) bound with slightly higher avidity than did the 2F5 mutatant peptide (containing the L669S mutation). Moreover, this hypothesis can not explain the similar fold of increase in the sensitivity of the TND_669S envelope to both 2F5 and 4E10 mAbs. Fourthly, the L669S mutation could have caused dramatic conformational change of Env, resulting in a more “open” MPER structure, and thus allowing for easier access of antibodies targeting 2F5 and 4E10. This hypothesis can very well explain the similar magnitude of increase in sensitivity of the TND_669S envelope to both 2F5 and 4E10 mAbs. The 447-52D sensitivity changes associated with the L669S mutation (>161×) suggests that the conformational change may have caused changes in the V3 loop as well. Steric constraints for neutralizing antibodies targeting MPER have been suspected by many groups. Several studies have observed possible antagonism between 2F5 and 4E10 (Zwick et al, J. Virol. 79:1252-1261 (2005), Nelson et al, J. Virol. 81:4033-4043 (2007)), suggesting that space limitation may be a factor affecting 2F5 and 4E10 neutralization of HIV virus. Interestingly, when 2F5 epitope was inserted to MLV Env (Ou et al, J. Virol. 80:2539-2547 (2006)), the Env with 2F5 epitope in surface unit is more than 10 times more sensitive to 2F5 neutralization than the Env with 2F5 epitope in the transmembrane unit. In addition, grafting 2F5 epitope into V1, V2, V4 regions of HIV Env also was shown to increase the binding of gp140 to 2F5 (Joyce et al, J. Biol. Chem. 277:45811-45820 (2002), and grafting 2F5 and 4E10 epitopes to the MPER of HIV-2 has been shown to be associated with substantial increase in 2F5-/4E10-neutralization sensitivity (Decker et al., presented at the Keystone Symposium on HIV Vaccines, Keystone Resort, Keystone, Colo., 2006), presumably through improved epitope accessibility. These data reflected the influence of epitope accessibility on 2F5 sensitivity. The characteristic of TND_669S is in concordance with a likely more “open” MPER structure.

The TND_669S isolate can be used to detect the presence of 2F5 and 4E10-like antibodies elicited by vaccination or natural infection (studies to date have failed to detect 2F5 or 4E10 in HIV-1 infected patients and vaccines). An ultra-sensitive isolate can provide crucial information as to whether or not 2F5/4E10 is generated at extremely low levels during natural infection or vaccination. Furthermore, the demonstration that a more exposed MPER, as TND_669S envelope appears to have, has significant applications for vaccine immunogen design.

EXAMPLE 2

Description of gp41MPER Peptide-Liposome Conjugates

FIG. 8 shows the amino acid sequences of each of the HIV-1 gp41MPER peptides that can be conjugated to synthetic liposomes. While these sequences have been used, longer gp41 sequences encompassing the entirety of the Heptad Repeat 2 (HR2) region (aa 637-683), as well as longer sequences involving the HR2 region as well as the HR1 region could be used (aa 549-602). The SP62 peptide presents the 2F5 mAb epitope while the MPER656 peptide includes both 2F5 and 4E10 mAb gp41 epitopes. (See WO 2008/127651.) Two variants of the MPER peptide sequences include the SP62-L669S and the MPER656-L669S. The L669S mutation was identified in an HIV-1 Envelope clone (TND_669S), obtained from a chronically infected HIV-1+ subject, that was highly sensitive to neutralization by both autologous and heterologous sera (see Example 1). TND_669S is highly sensitive (with $IC_{50}$ about 300-fold lower when compared to TND_669L) to neutralization by both 2F5 and 4E10 mAbs (Shen J. Virology 83: 3617-25 (2009)). The mutation resulted in more favorable mAb binding kinetics with significantly slower off-rates of the mAb 2F5-peptide liposome complex (SP62-L669S peptide-liposomes). Tryptphan (W) immersion depth analysis of SP62-liposomes suggested that the L669S substitution could alter the orientation of the core 2F5 and 4E10 epitopes and make them more accessible for B cell recognition. Thus, the use of L669S substitution in both forms of liposomes with SP62-L669S and MPER656-L669S peptides afford novel immunogens with favorably exposed core MPER neutralizing epitopes and the potential for the induction of neutralizing antibodies following immunization.

Description of gp41 MPER Peptide-Adjuvant Conjugates

Toll-like receptor ligands, shown in FIG. 9, were formulated in liposomal forms with gp41MPER peptide immunogens. The ligands referenced in FIG. 9 are examples only and other forms of TLR agonists (Takeda et al, Annu. Rev. Immunol., 21:335-376 (2003)) can be incorporated into similar liposomes as well.

The construction of Lipid A and R-848 containing MPER peptide liposomes utilized the method of co-solubilization of MPER peptide having a membrane anchoring amino acid sequence and synthetic lipids 1-Palmitoyl-2-Oleoyl-sn-Glycero-3-Phosphocholine (POPC), 1-Palmitoyl-2-Oleoyl-sn-Glycero-3-Phosphoethanolamine (POPE), 1,2-Dimyristoyl-sn-Glycero-3-Phosphate (DMPA) and Cholesterol at mole fractions 0.216, 45.00, 25.00, 20.00 and 1.33 respectively (Alam et al, J. Immunol. 178:4424-4435 (2007)). Appropriate amount of MPER peptide dissolved in chloroform-methanol mixture (7:3 v/v), Lipid A dissolved in Chloroform or R-848 dissolved in methanol, appropriate amounts of chloroform stocks of phospholipids were dried in a stream of nitrogen followed by over night vacuum drying. Liposomes were made from the dried peptide-lipid film in phosphate buffered saline (pH 7.4) using extrusion technology.

Construction of oligo-CpG complexed MPER peptide liposomes used the cationic lipid 1-Palmitoyl-2-Oleoyl-sn-Glycero-3-ethylphospho choline (POEPC) instead of POPC. Conjugation of oCpG was done by mixing of cationic liposomes containing the peptide immunogen with appropriate amounts of oCpG stock solution (1 mg/ml) for the desired dose.

Surface Plasmon Resonance (SPR) assay for the binding of 2F5 mAb to its epitope in the peptide-liposome constructs revealed that incorporation or conjugation of TLR adjuvants does not affect binding of HIV neutralizing antibody 2F5. Strong binding of both mAbs 2F5 and 4E10 were observed.

EXAMPLE 3

Figure 13:
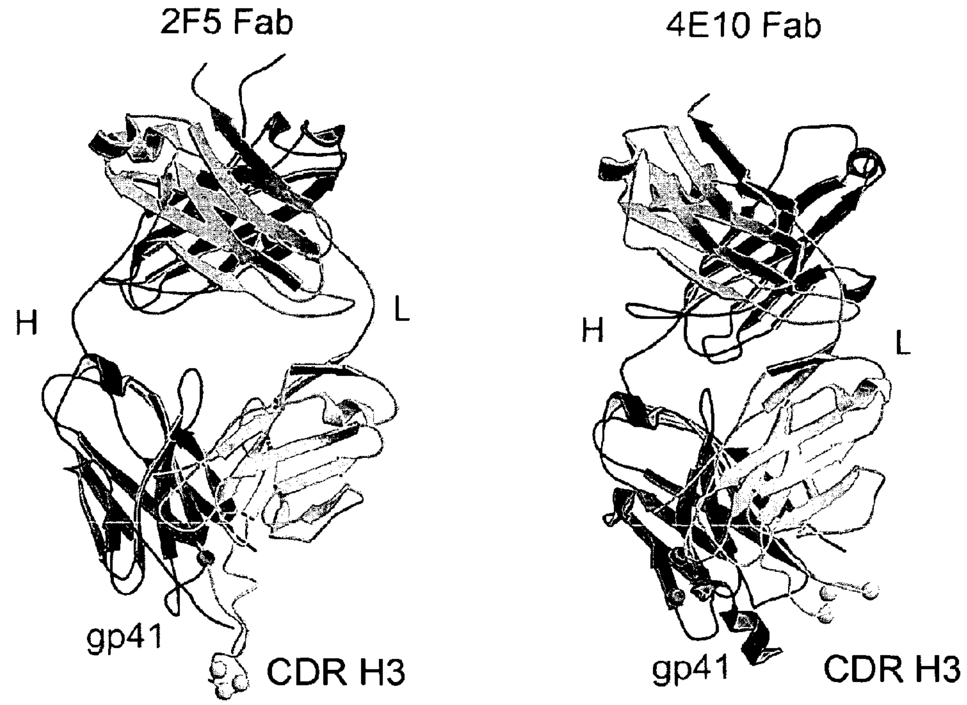
FIG. 13. Crystal structures of 2F5 (Ofek et al, J. Virol. 78:10724 (2004)) and 4E10 (Cardoso et al, Immunity 22:163-173 (2005)) and design of mutations in the CDR H3 loop to eliminate binding to lipids and HIV-1 viral membrane.
Figure 14A:
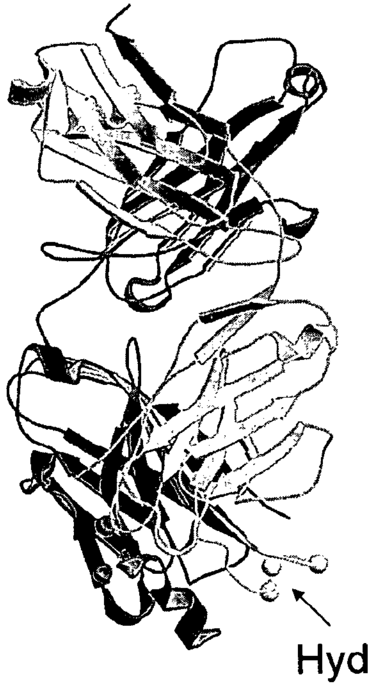
FIGS. 14A and 14B. Substitution of hydrophobic residues of 4E10 (FIG. 14A) and 2F5 (FIG. 14B) CDR H3 disrupt lipid binding and abrogate ability of both mAbs to neutralize HIV-1.
Figure 14B:
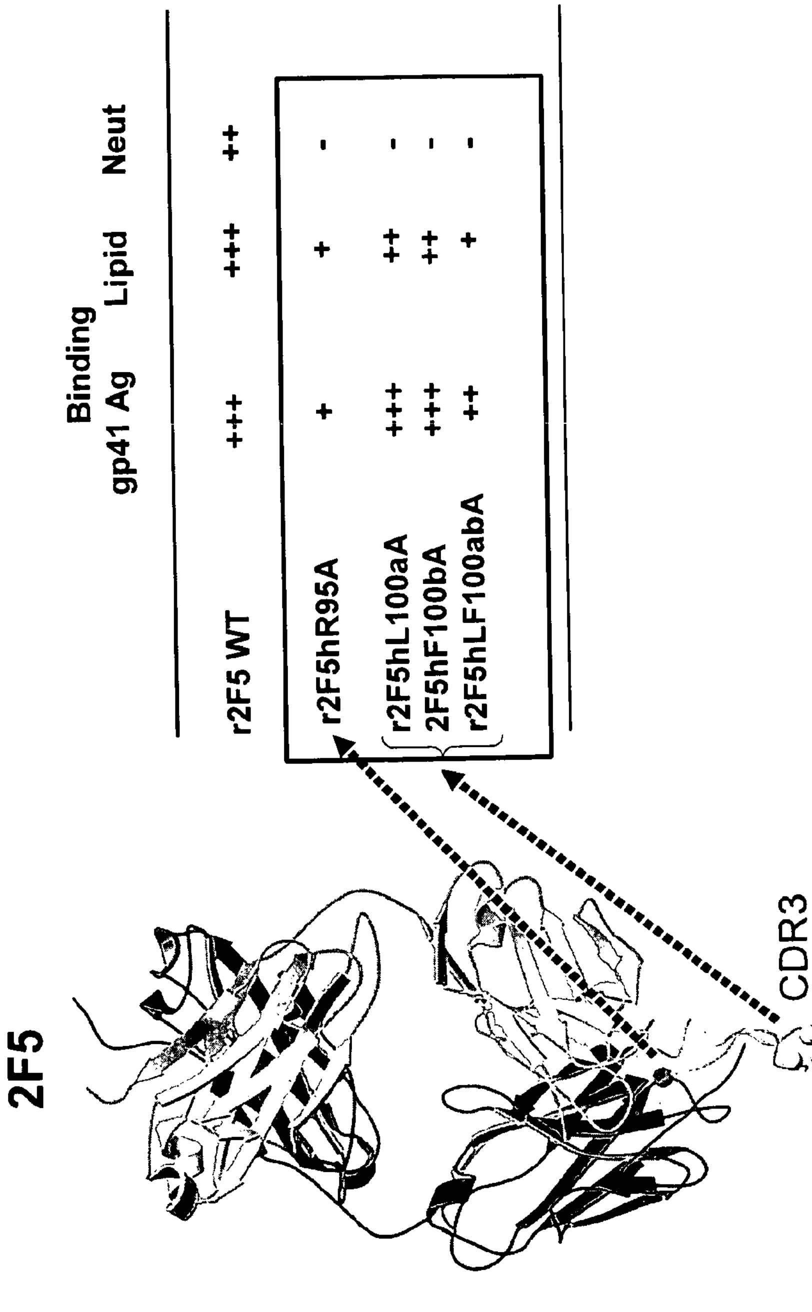

The long CDR H3 loops of MPER neutralizing mAbs 4E10 and 2F5 have a hydrophobic face, postulated to interact with virion membrane lipids (Ofek et al, J. Virol. 78:10724 (2004); Cardoso et al, Immunity 22:163-173 (2005)). CDRH3 mutants of 4E10 (scFv) and 2F5 (IgG) have been constructed (see FIG. 13) and it has been found that binding of neutralizing MPER mAbs occur sequentially and is initiated by binding of mAbs to viral membrane lipids prior to binding to prefusion intermediate state of gp41. 4E10 scFv bound strongly to both nominal epitope peptide and a trimeric gp41 fusion intermediate protein, but bound weakly to both HIV-1 and SIV virions and thus indicating that 4E10 bound to viral membrane lipids and not to the prefusion state of gp41. While alanine substitutions at positions on the hydrophobic face of the CDR H3 loops of 4E10 (W100a/W100b/L100cA) showed similar binding to gp41 epitopes, the same substitutions disrutpted the ability of 4E10 to bind to HIV-1 viral membrane (FIG. 14). 4E10 CDR H3 mutants that bound to gp41 intermediate protein but did not bind to HIV-1 viral membrane failed to neutralize HIV-1. Similarly, 2F5 CDR H3 mutants with disruptions in binding to HIV-1 virions but not to gp41 epitope peptide, failed to neutralize HIV-1 (FIG. 14). Blocking of HIV-1 neutralization activity of 4E10 by gp41 fusion intermediate protein further suggested that 4E10 did not bind to viral prefusion gp41. These results support the model that binding of neutralizing MPER mAbs occurs sequentially and is initiated by binding of mAbs to viral membrane lipids prior to binding to prefusion intermediate state of gp41. An important implication of this result is that the HIV-1 membrane constitutes an additional structural component for binding and neutralization by 4E10 and 2F5. Thus, a lipid component may be required for an immunogen to induce 4E10 and 2F5-like antibody responses.

Thus, this strategy has the potential to modulate B cell tolerance, target immunogens to responsive B cell subsets, and allow the induction of polyreactive B cells that bind to phospholipids and gp41MPER epitopes. When used in combination with TLR ligands, the delivery of IFN-α in liposomes has the potential to allow TLR-dependent activation of B cells from the autoreactive pool and with the desired specificity for gp41MPER epitopes.

Figure 11:
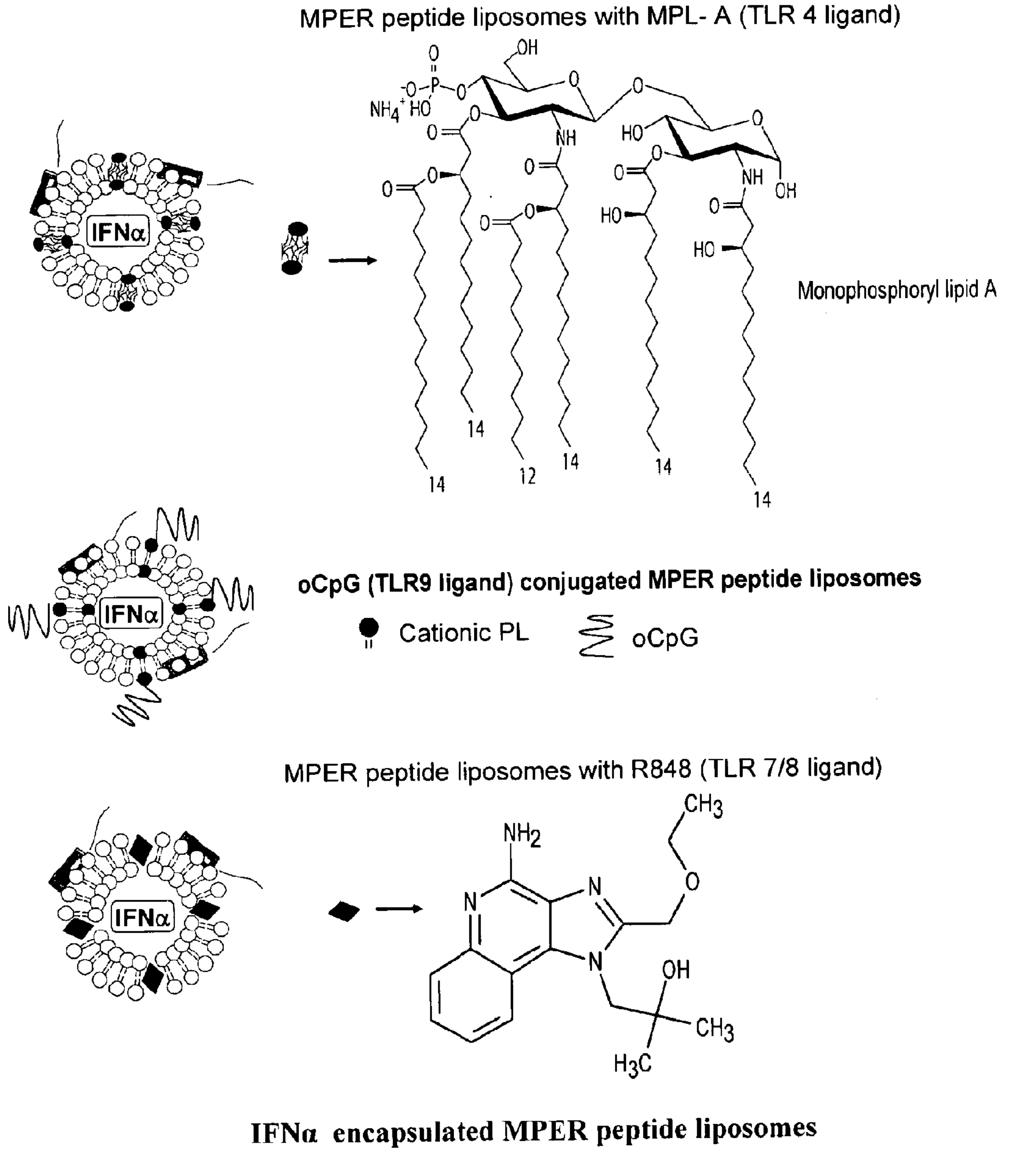
FIG. 11. IFNα encapsulated MPER peptide liposomes
Figure 12:
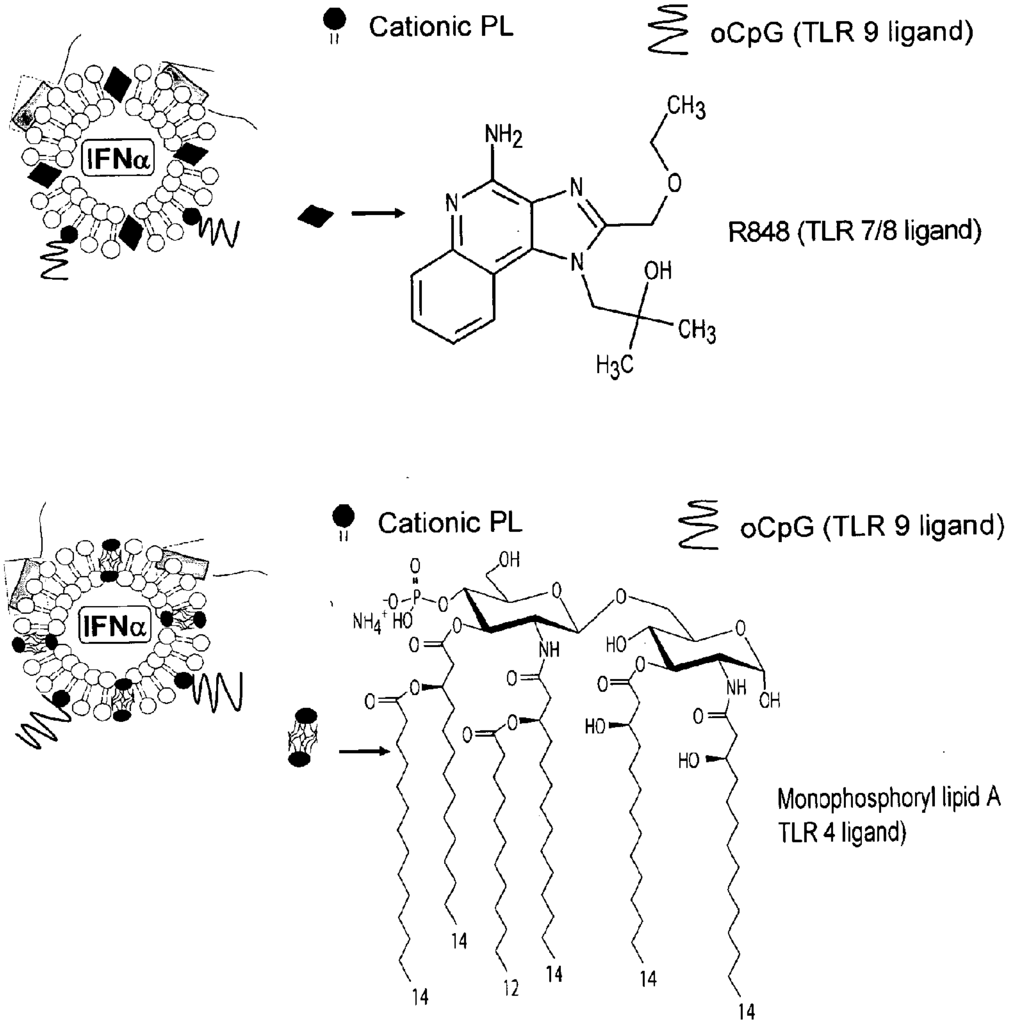
FIG. 12. IFNα encapsulated liposome with multiple TLR ligands. These constructs have the potential to provide synergy in B cell responses via dual TLR triggering.

Description of Constructs:

The HIV-1 gp41MPER peptides (FIG. 8) can be conjugated to synthetic liposomes as outlined above and described previously (Alam et al, J. Immunol. 178:4424-4435 (2007)). Each of the sonicated MPER peptide-liposomes can be prepared and then mixed with soluble IFNα protein and then dried and rehydrated to encapsulate the cytokine. After brief vortexing, the rehydrated liposomes with encapsulated IFNa can be collected by ultracentrifugation for 30 min. In a first design, liposome is conjugated to either oCpG (TLR9), MPL-A (TLR4) or R848 (TLR7/9) (FIG. 11). Each of these adjuvanted liposome constructs can be prepared with each of the listed MPER peptides shown in FIG. 8. A second design is shown in FIG. 12 and includes multiple TLR ligands, TLR9+TLR4 and TLR9+TLR7/8 incorporated into the same liposomes. The design of these constructs can provide synergy in TLR triggering and potentially enhance the potency of the TLR ligands in activating polyreactive B cells.

Figures 10A, 10B, 10C:
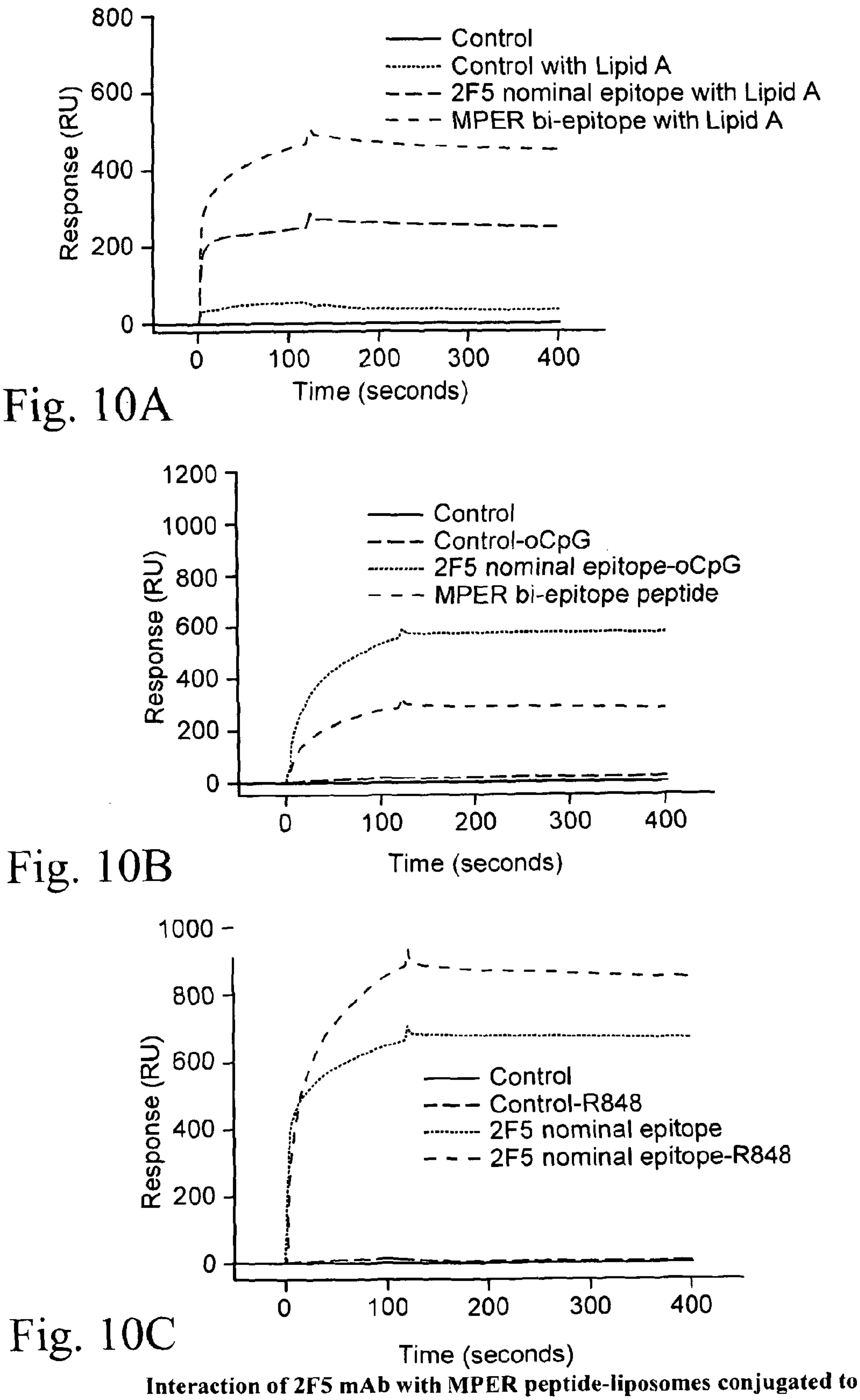
FIGS. 10A-10C. Interaction of 2F5 mAb with MPER peptide-liposomes conjugated to TLR adjuvants.

The assessment of the presentation of MPER epitopes on the adjuvanted liposome constructs can be done by SPR analysis of 2F5 and 4E10 mAb binding as described in FIG. 10.

EXAMPLE 4

Experimental Details

Figure 17:
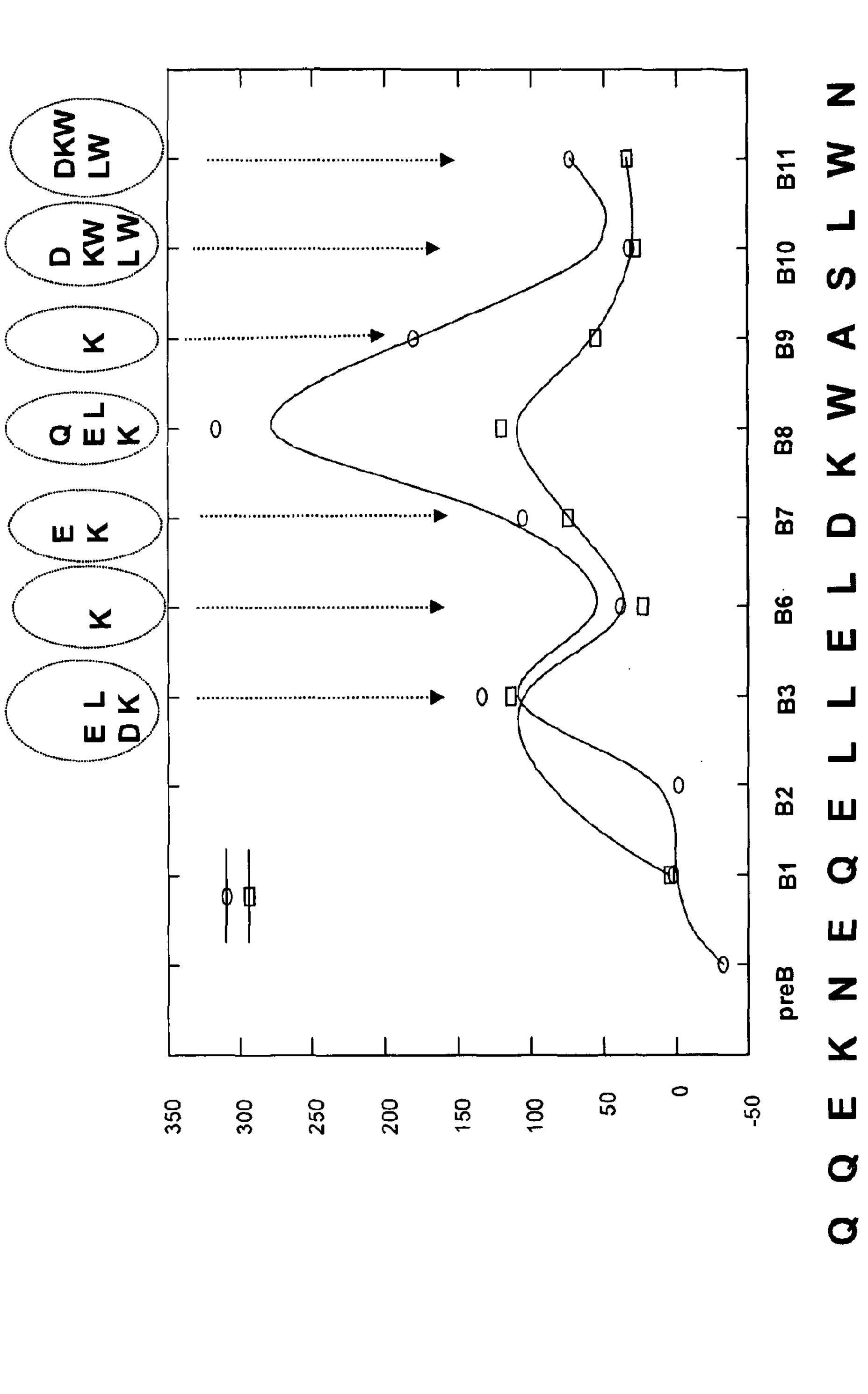
FIG. 17. Induction of gp41 MPER specific antibody (SEQ ID NO: 9) responses in guinea pigs immunized with MPER liposomal immunogens.

Representative data from two immunized animals show the application of a prime/boost strategy for the induction of MPER specific antibody responses following repeated immunizations with MPER peptide liposomes (see FIG. 17). The animals were immunized at alternating and at regular interval first with SP62 liposomes (4×), and then with Env gp140 (2×) protein. The final two immunizations include the full length MPER-656 liposomes (see description of immunogens above). Binding responses in immunized sera were measured by SPR analyses of binding to MPER peptide with the shown sequence. Bleed samples from each immunized animals were collected at the indicated post-bleed time points. Epitope mapping of the immunized sera was done on the BIAcore A100 using biotinylated alanine substituted MPER peptides with single amino acid substitution of each MPER residue. Residues circled on top indicate the critical residues (in red (underlined) with >50% reduction in binding to alanine substituted peptide) required for binding to the MPER peptide. Residues in blue (not underlined) indicate residues with lower degree of involvement (<20-50% reduction in binding).

Results

The presented experimental data shows the application of the designed MPER liposomal immunogens in the induction of antibodies that are targeted to the neutralizing epitopes on gp41 of HIV-1 Envelope protein. The data shows that the constructed MPER peptide liposomes are immunogenic in small animals like guinea pigs and non-human primates (NHP) and that the induced antibody responses are specific for the core neutralizing epitope on gp41MPER. These studies also demonstrate the application of prime-boost strategy in enhancement of the MPER specific responses and in focusing of the antibody responses to the core neutralizing epitopes that include the 2F5 core residues DKW. In the presented immunization scheme, the data shows a shift in the binding epitope in initial responses from residues that are N-terminus to the core DKW to responses that include all three residues of the core neutralizing epitope (DKW) that are induced in later time points. Final immunizations with the MPER liposomes resulted in focusing of the antibody responses to the core DKW residues of the broad neutralizing mAb 2F5. These data represents application of the design of MPER immunogens in liposomal form for the induction of MPER specific antibodies in experimental animals like guinea pigs (FIG. 17) and NHP (FIG. 18). Such MPER immunogen designs can be candidates for human trials.

EXAMPLE 5

Figure 18A:
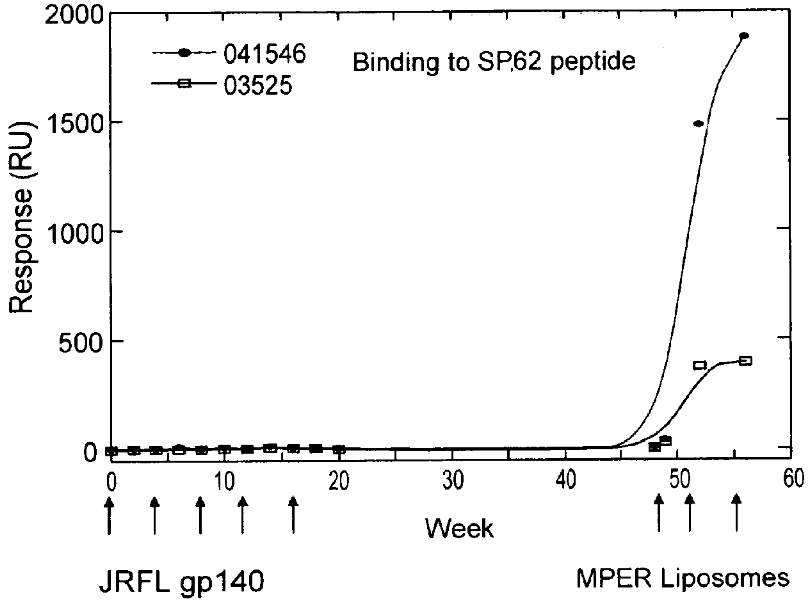
FIG. 18. Induction of gp41MPER specific antibody responses in Non human primates (NHP) immunized with MPER liposomal immunogens.

As shown in FIG. 18A, MPER specific binding responses were not induced following priming with gp140 Env protein but were induced following boosting with MPER liposomes. No binding responses to MPER peptides were detected following multiple immunizations with gp140 protein. Boosting of the same animals with MPER-656 liposomes resulted in MPER specific responses that were specific for the 2F5 nominal epitope peptide.

Figure 18B:
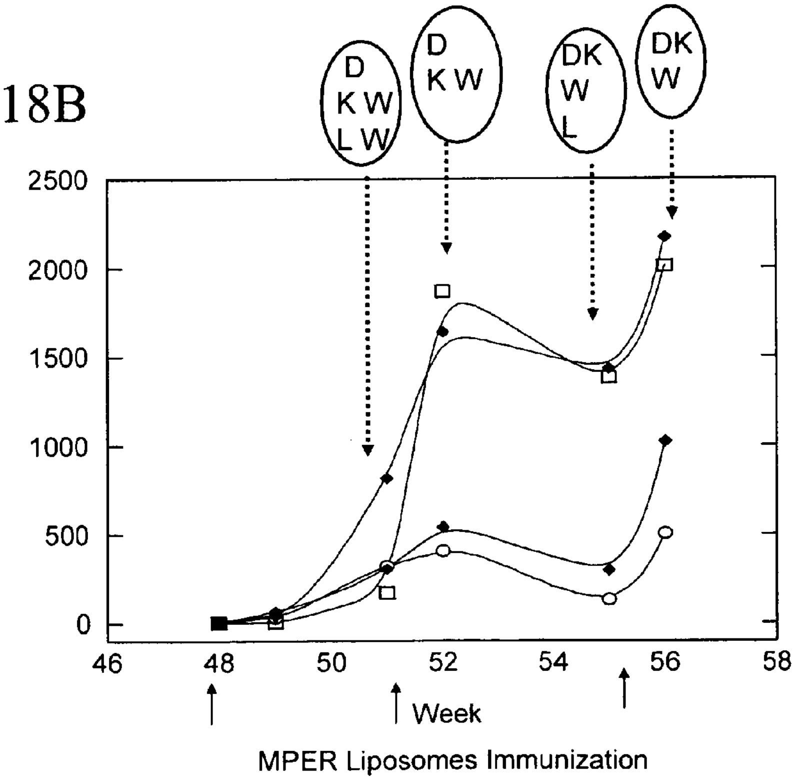

As shown in FIG. 18B, epitope mapping of the antibody responses show focusing of the response to the neutralizing 2F5 core residues DKW. An initial broader specificity was focused to the DKW core residues after the third immunization.

Binding data from four NHP immunized sera are shown. Binding response measurements and epitope mapping experiments were done as described in FIG. 17.

* * *

All documents and other information sources cited above are hereby incorporated in their entirety by reference.

What is claimed is:

1. A method of inducing the production in a subject of anti-HIV-1 antibodies comprising administering to said subject a composition comprising a liposome-peptide conjugate in an amount sufficient to effect said induction, wherein said peptide comprises SEQ ID NO:17 (NEQELLELDKWASSWNWFNITNWLWYIK) presented on the surface of said liposome.

2. The method according to claim 1 wherein said peptide further comprises a hydrophobic linker.

3. The method according to claim 2 wherein said linker is C-terminal to said MPER epitope.

4. The method according to claim 2 wherein said linker is GTH1.

5. The method according to claim 1 wherein said peptide is NEQELLELDKWASSWNWFNITNWLWYIK (SEQ ID NO: 17) presented on the surface of the liposome via the GTH1 linker.

6. The method according to claim 1 wherein the composition further comprises an adjuvant.

7. The method according to claim 6 wherein said adjuvant is a Toll Like Receptor (TLR) ligand.

8. The method according to claim 7 wherein said TLR ligand is a TLR9 ligand.

9. The method according to claim 8 wherein said TLR9 ligand is oligo CpG.

10. The method according to claim 7 wherein said TLR ligand is a TLR7/8 ligand.

11. The method according to claim 10 wherein said TLR7/8 ligand is R-848.

12. The method according to claim 7 wherein said TLR ligand is a TLR4 ligand.

13. The method according to claim 12 wherein said TLR4 ligand is monophosphorylipid A.

14. The method according to claim 7 wherein said conjugate comprises a TLR9 ligand and a TLR7/8 ligand.

15. The method according to claim 14 wherein said TLR9 ligand is oligo CpG and said TLR7/8 ligand is R-848.

16. The method according to claim 7 wherein said conjugate comprises a TLR9 ligand and a TLR4 ligand.

17. The method according to claim 16 wherein said TLR9 ligand is oligo CpG and said TLR4 ligand is R-848.

18. The method according to claim 7 wherein said composition further comprises interferon-αencapsulated therewithin.

19. The method according to claim 7 wherein said composition is administered as a prime or a boost.

20. A composition comprising a liposome and an MPER peptide comprising the peptide of SEQ ID NO:17, wherein the peptide is presented on the surface of the liposome via a hydrophobic linker.

21. The composition according to claim 20 further comprising interferon-α encapsulated within said liposome.

22. The composition of claim 20 further comprising an adjuvant.

23. The composition of claim 21, wherein the adjuvant is a Toll Like Receptor (TLR) ligand.

24. The composition of claim 21, wherein the TLR ligand is TLR4, TLR7/8, TLR9, or any combination thereof.

25. The composition of claim 24, wherein the TLR4 ligand is monophosphorylipid A.

26. The composition of claim 24, wherein the TLR7/8 ligand is R848.

27. The composition of claim 24, wherein the TLR9 ligand is oligoCpG.

28. The composition of claim 24, wherein the linker is GTH1.

* * * * *